US006498948B1

United States Patent
Ozawa et al.

(10) Patent No.: US 6,498,948 B1
(45) Date of Patent: Dec. 24, 2002

(54) ENDOSCOPE SYSTEM

(75) Inventors: Ryo Ozawa, Tokyo (JP); Tetsuya Nakamura, Saitama-ken (JP); Tetsuya Utsui, Saitama-ken (JP); Shinsuke Okada, Saitama-ken (JP); Masaru Eguchi, Tokyo (JP); Koichi Furusawa, Tokyo (JP)

(73) Assignee: Pentax Corporation, Tokyo (JP)

( * ) Notice: Subject to any disclaimer, the term of this patent is extended or adjusted under 35 U.S.C. 154(b) by 220 days.

(21) Appl. No.: 09/641,885

(22) Filed: Aug. 18, 2000

(30) Foreign Application Priority Data

Aug. 25, 1999  (JP) .......................................... 11-237825

(51) Int. Cl.[7] ................................................ A61B 6/00
(52) U.S. Cl. ........................ 600/476; 600/478; 356/345
(58) Field of Search ................................ 600/476, 478, 600/160; 356/345; 348/65, 68, 77

(56) References Cited

U.S. PATENT DOCUMENTS

| 4,556,057 | A | * | 12/1985 | Hiruma et al. .............. 600/476 |
| 5,321,501 | A |   | 6/1994 | Swanson et al. |
| 6,069,698 | A |   | 5/2000 | Ozawa et al. |
| 6,293,911 | B1 | * | 9/2001 | Imaizumi et al. ........... 600/160 |
| 2002/0052547 | A1 | * | 5/2002 | Toida ......................... 600/425 |

FOREIGN PATENT DOCUMENTS

| JP | 6-154228 | 6/1994 |
| JP | 11-56751 | 3/1999 |
| JP | 11-56752 | 3/1999 |

OTHER PUBLICATIONS

Article entitled "In Vivo Endoscopic OCT Imaging of Precancer and Cancer States of Human Mucosa", by Segeev et al., Optics Express, vol. 1, No. 13, Dec. 22, 1997, pp. 432–440.

G.J. Tearney et al., *In Vivo Endoscopic Optical Biopsy with Optical Coherence Tomography*, Science, vol. 276, Jun. 27, 1997, pp. 2037–2039.

* cited by examiner

*Primary Examiner*—George Manuel
*Assistant Examiner*—Shawna J. Shaw
(74) *Attorney, Agent, or Firm*—Greenblum & Bernstein, P.L.C.

(57) ABSTRACT

An endoscope system is provided with a normal light image capturing system, a fluorescent light image capturing system, and an OCT (Optical Coherence Tomography) image capturing system. The normal light image, the fluorescent light image and the OCT image are displayed on a screen of a display device simultaneously. Optionally, one of the normal light image or the fluorescent light image is displayed as an animated image, and the OCT image is also displayed as an animated image. A cursor indicating a scanning position corresponding to the OCT image is indicated on one of the normal light image and the fluorescent light image displayed as the animated image.

15 Claims, 14 Drawing Sheets

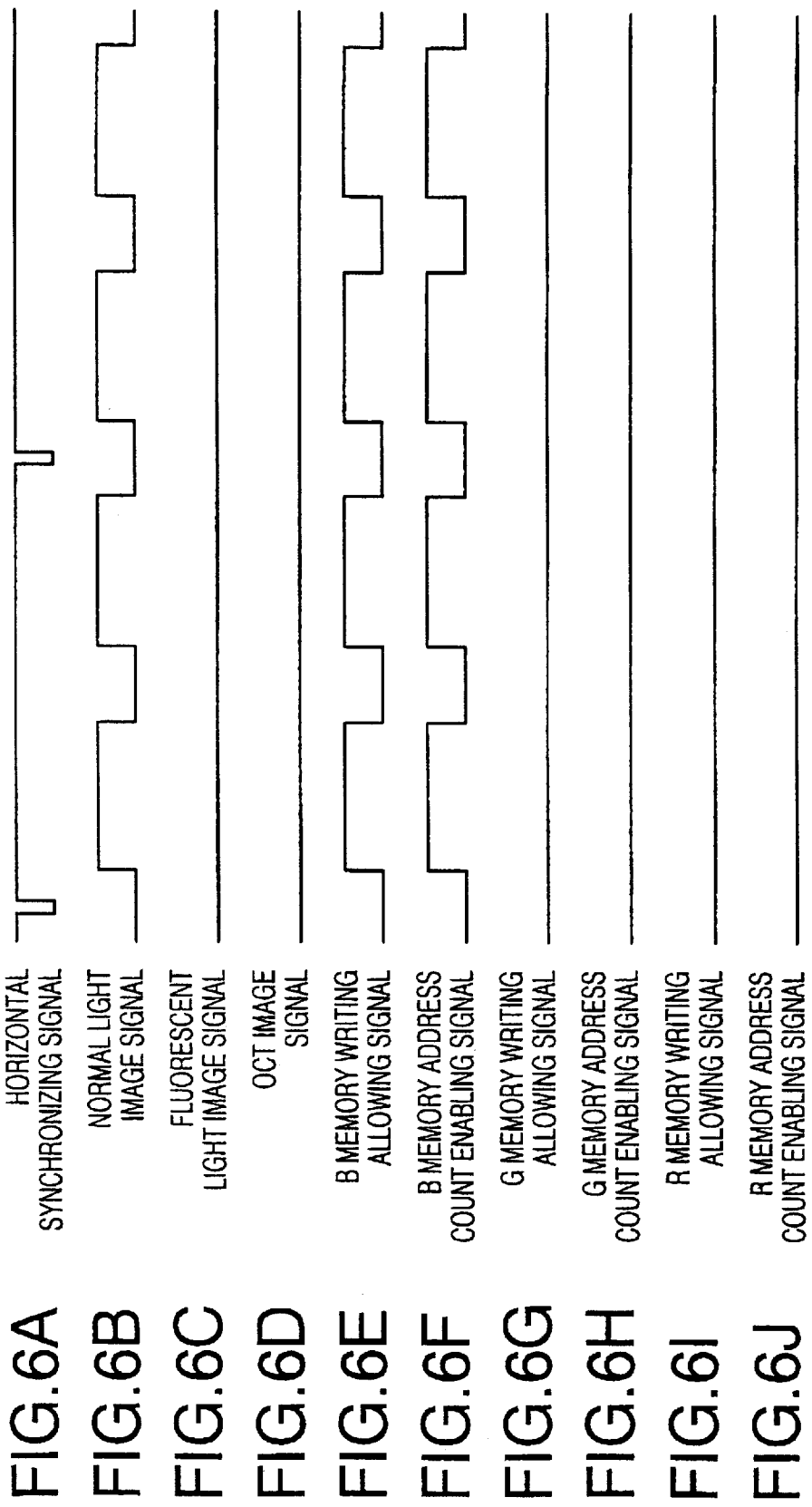

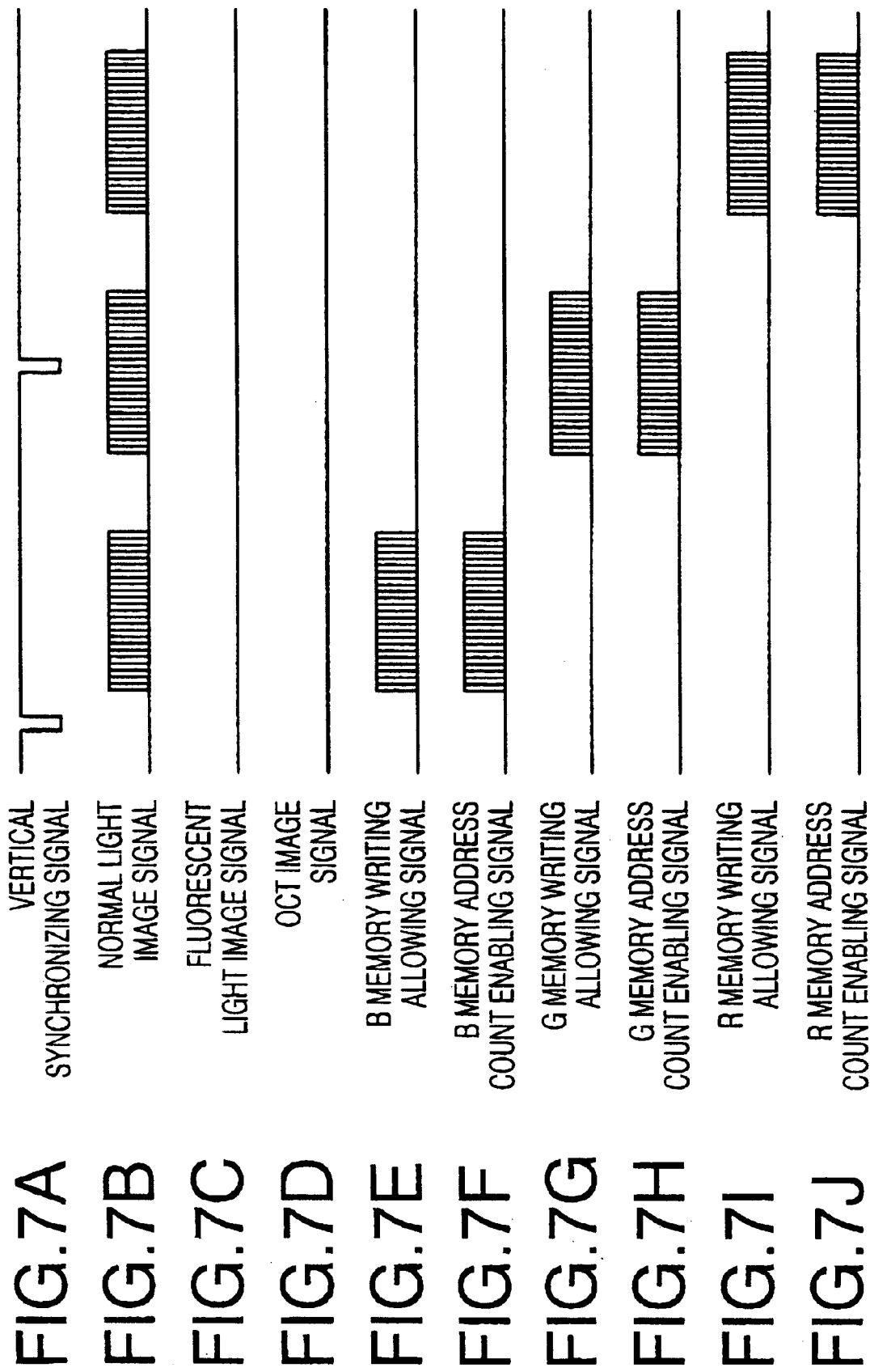

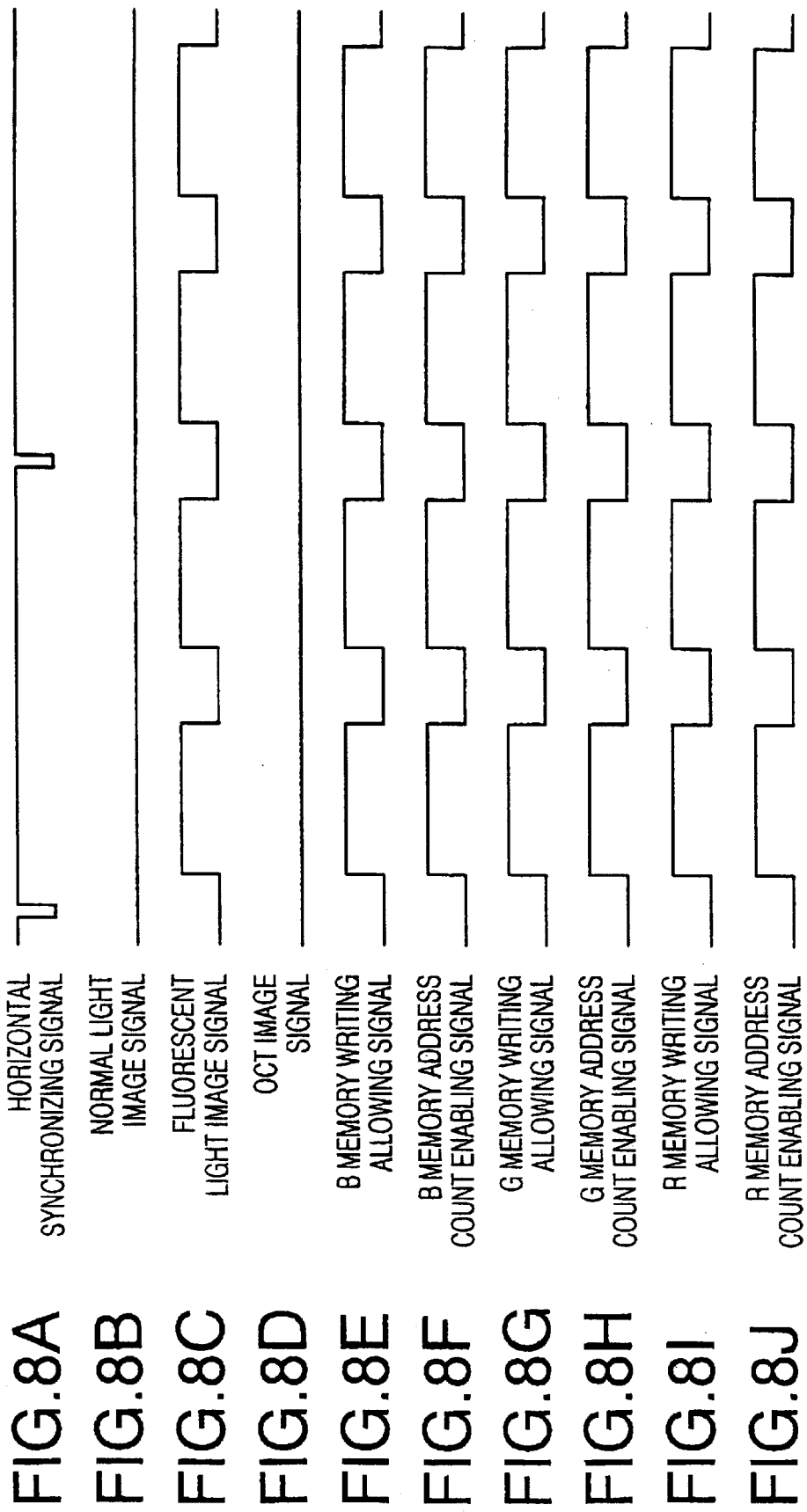

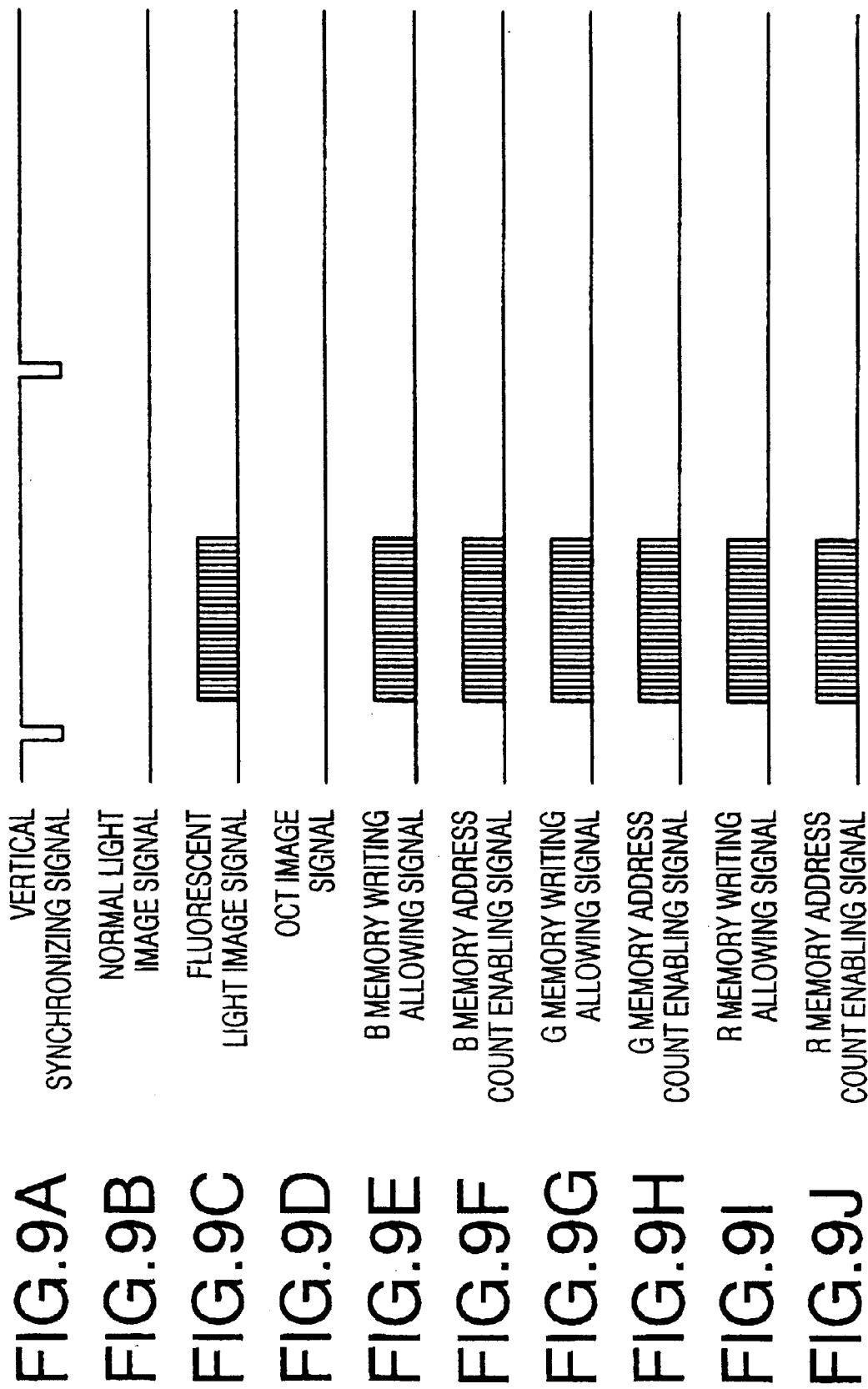

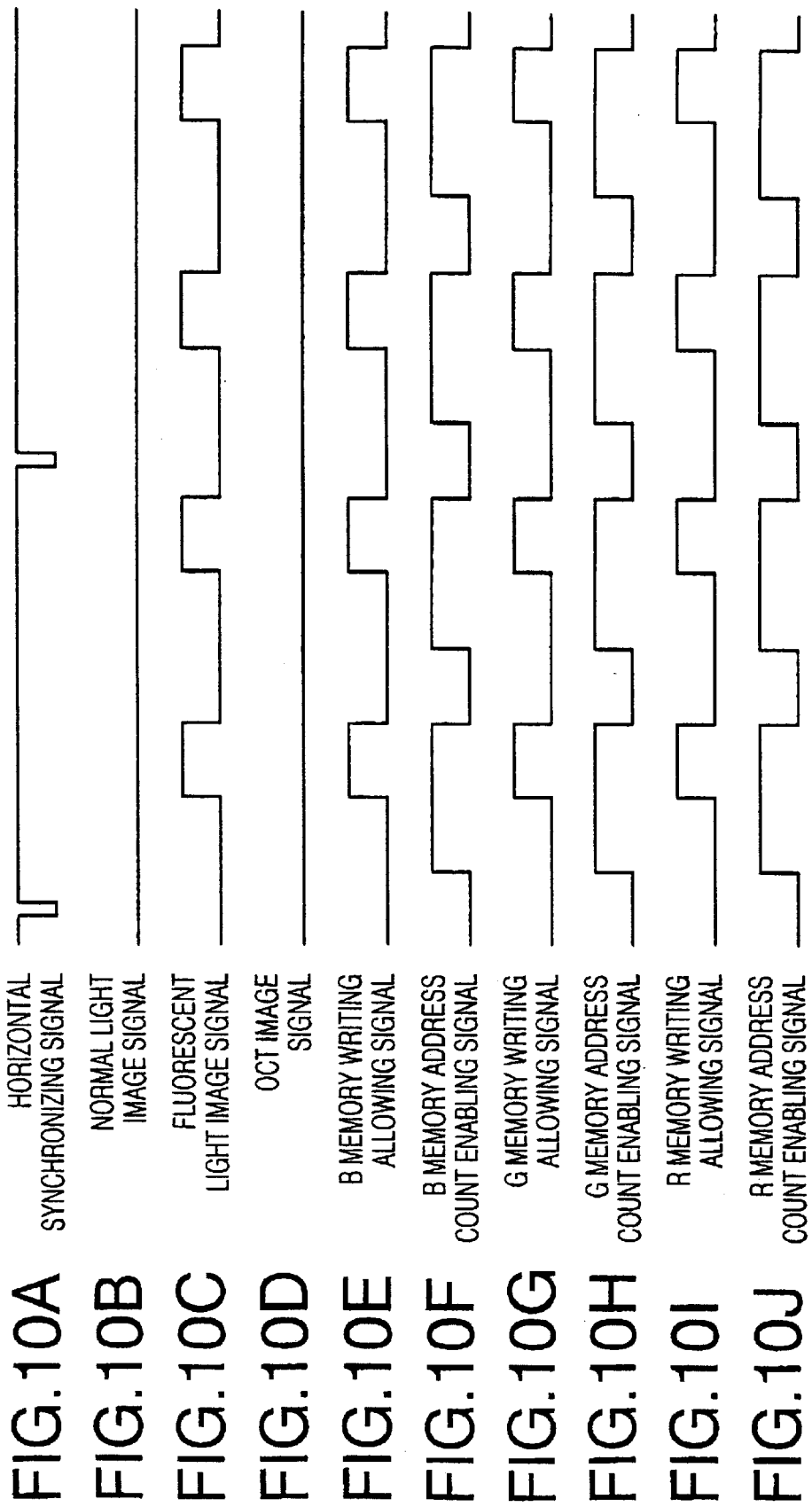

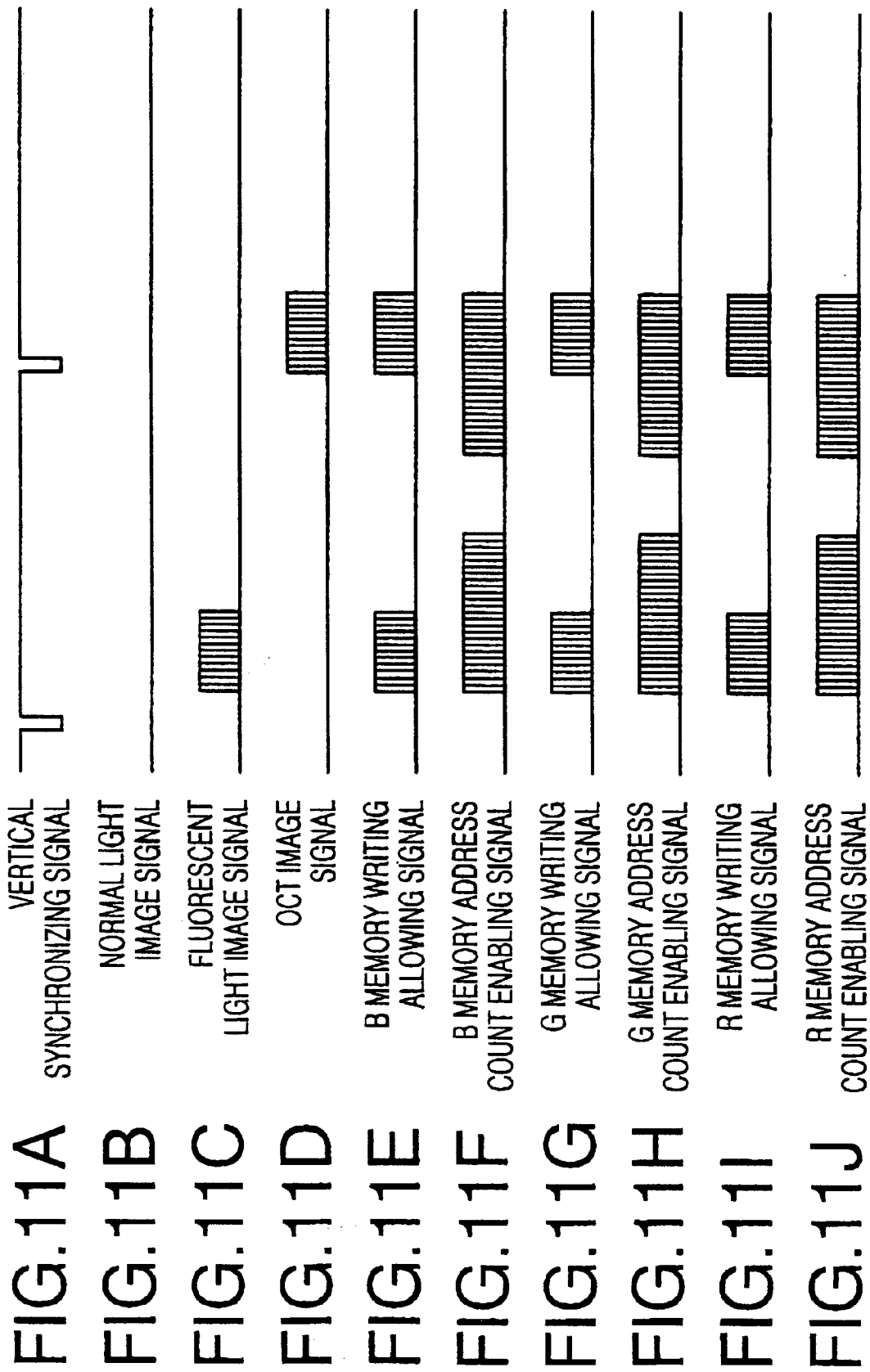

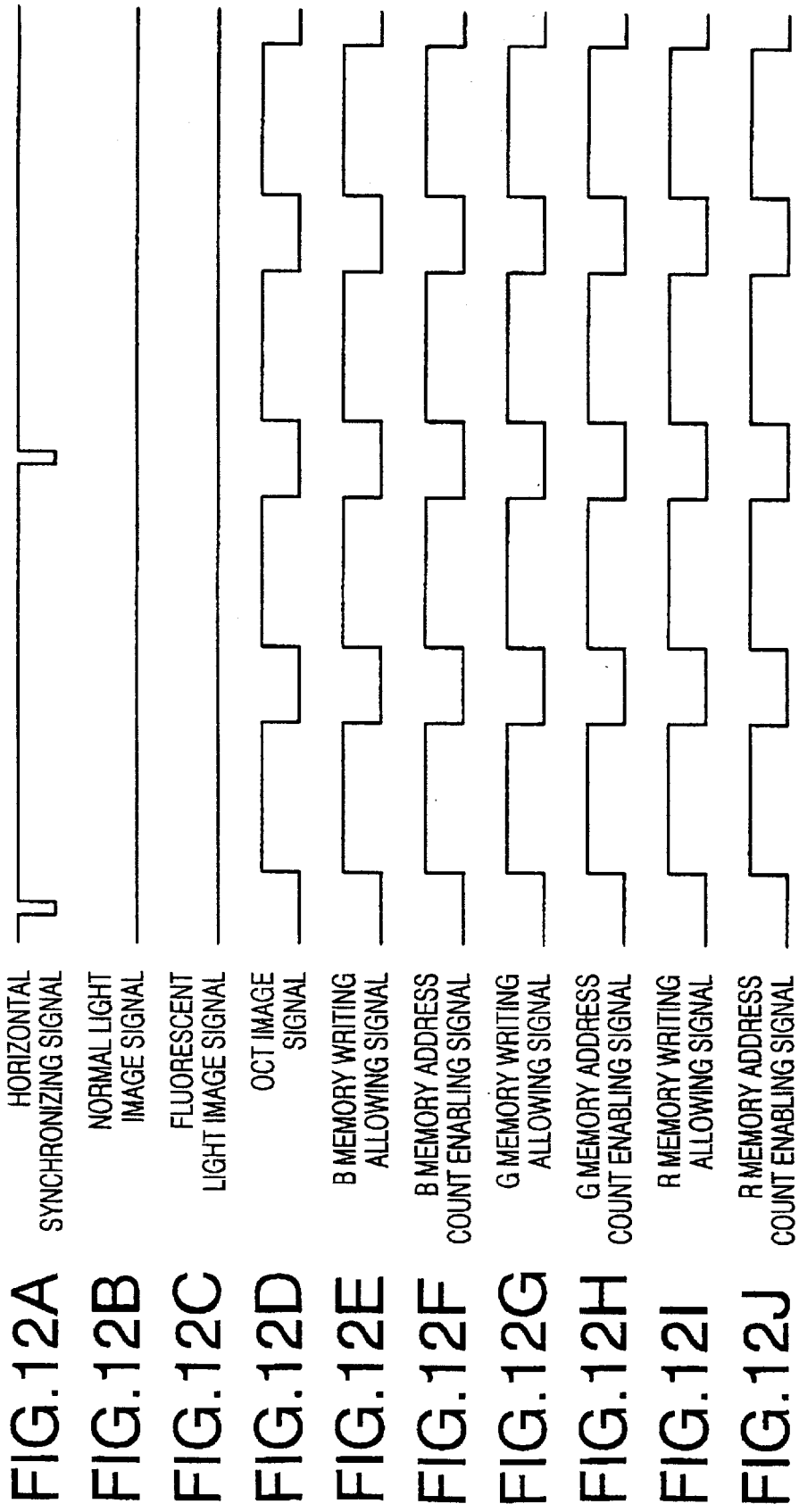

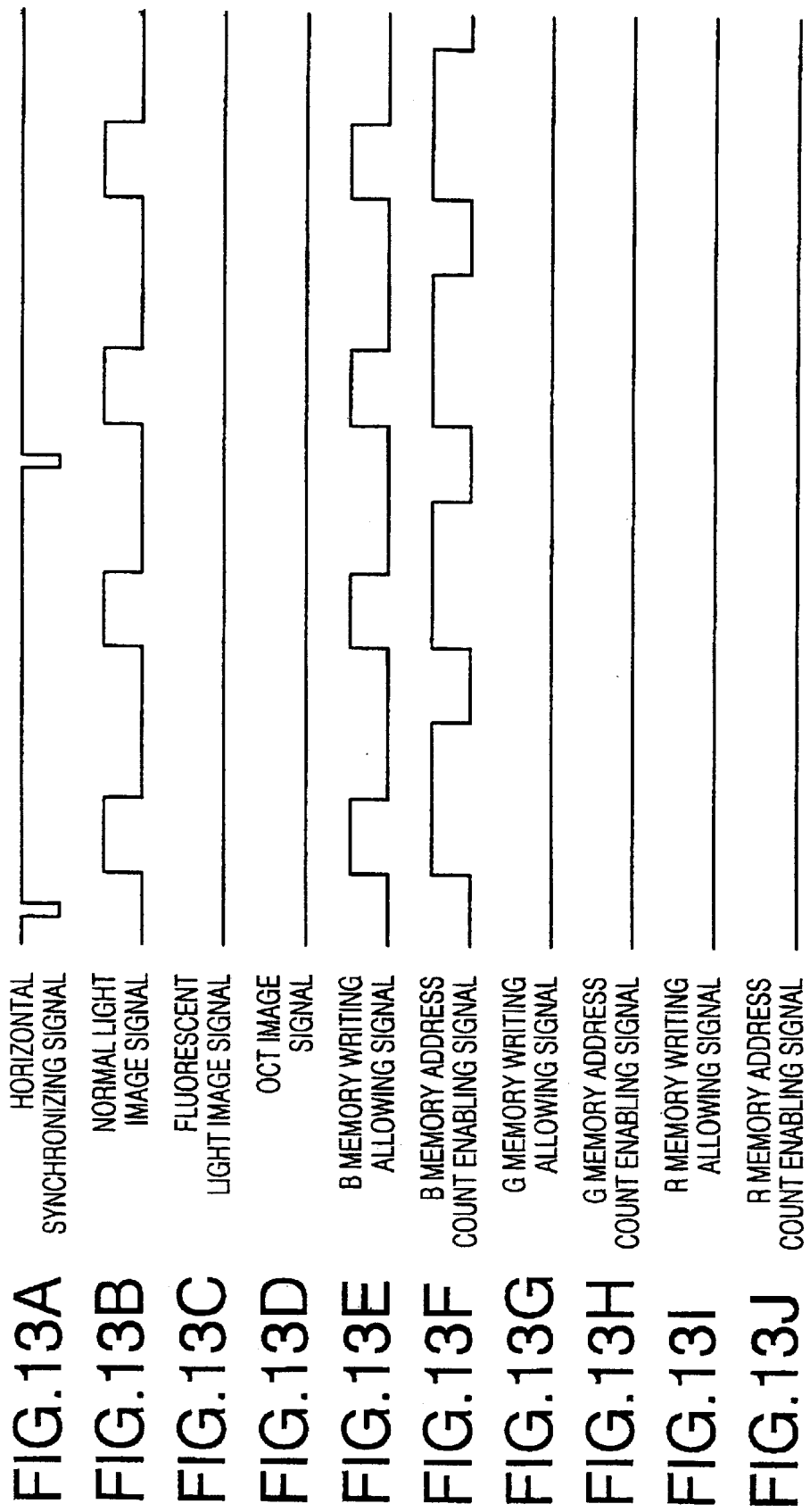

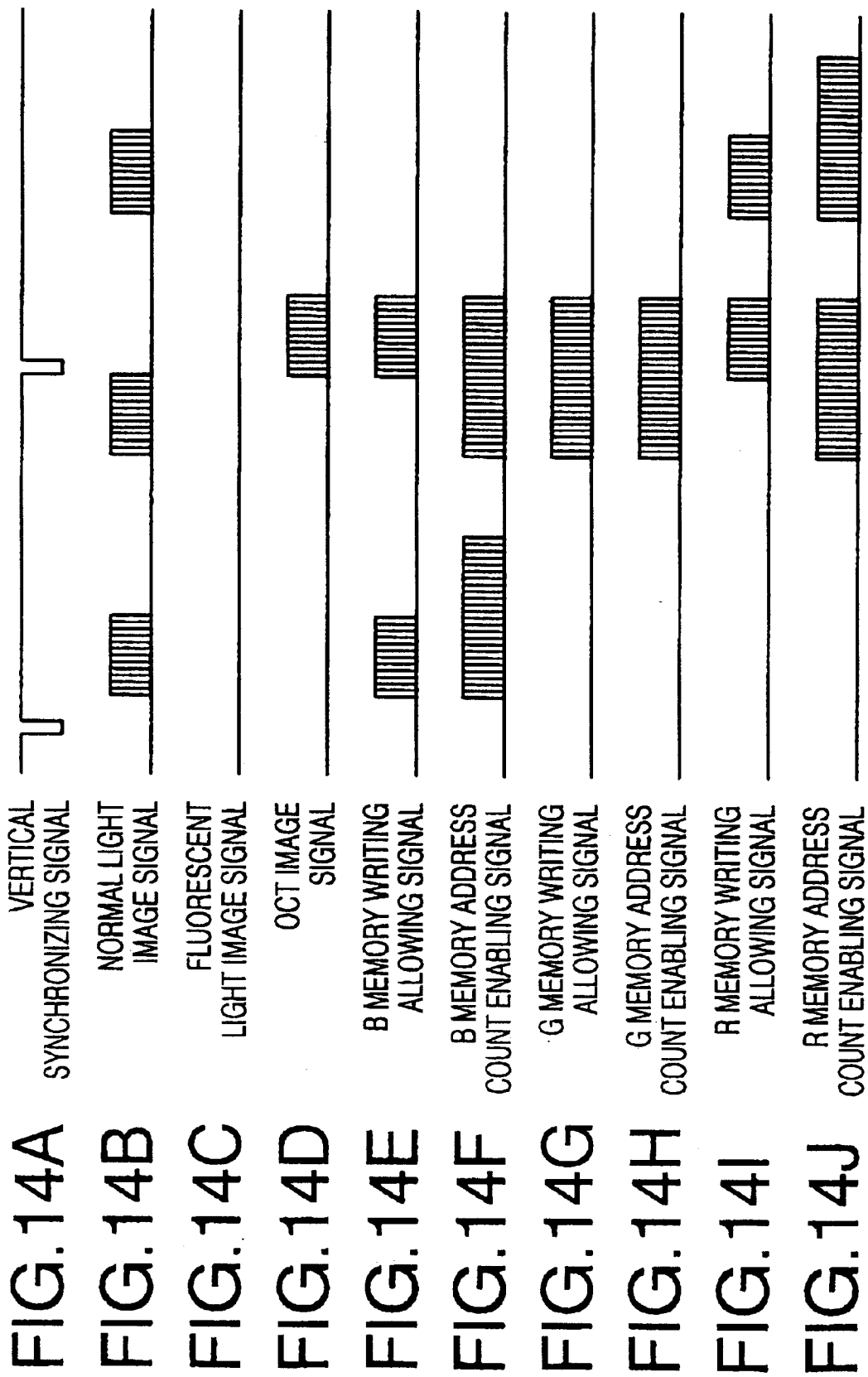

ENDOSCOPE SYSTEM

BACKGROUND OF THE INVENTION

The present invention relates to an endoscope system that is capable of capturing OCT (Optical Coherence Tomography) images of an object such as biotissues as well as normal light and/or fluorescent light images of a surface of the object.

Conventionally, endoscope systems for observing objects inside a human cavity have been known. An endoscope system is generally provided with an endoscope, which is to be inserted inside the human cavity, and an illuminative external device, which is to be connected to the endoscope. The external device includes a light source unit for illuminating the object, and a processor for processing image signals.

The endoscope includes:

an illuminating optical system, which is connected to the light source unit of the illuminative external device and used for illuminating an object (e.g., the paries of a body cavity);

an objective optical system for receiving light from the object and forming an optical image of the object; and a CCD (Charge Coupled Device) provided substantially at a focal plane of the objective optical system for capturing the object image, the CCD being electrically connected to the processor of the external device.

At a tip end of the endoscope, an instrument opening is formed. Forceps or various kinds of treatment instruments can be inserted through the endoscope, and the tip portion of the inserted instrument is protruded from the instrument opening, inside the human cavity.

With the endoscope system described above, an operator is capable of observing inside the human cavity as described below.

The operator firstly inserts the endoscope inside the human cavity. Light emitted by the light source unit of the external device is projected to an object to be observed through the illuminating optical system. An optical image of the illuminated object is formed, through the objective optical system, on the light receiving surface of the CCD. The CCD converts the received optical image into an electronic image (i.e., image signal), which is transmitted to the processor of the external device. The processor processes the received image signal, and displays the image of the object on a displaying device. Thus, the operator is capable of observing, for example, the paries of the human cavity of a patient by viewing the images displayed on the displaying device.

If the operator judges that there is a possibility of a cancer or a tumor within the observing portion of the human cavity, a forceps or biopsy instrument is inserted in an instrument channel inside the endoscope. The tip portion of the instrument is protruded from the instrument opening, and the tissues of the portion in question can be collected. The tissues thus obtained is subjected to a pathological inspection, and based on the results of the inspection, diagnosis is made.

According to the conventional endoscope system as described above, only the surface (i.e., paries) of the human cavity is observable. In order to know the condition of tissues beneath the paries of the human cavity, biopsy operation is required. In particular, in order to find an early cancer or a small tumor, the biopsy operation is indispensable. However, the pathological inspection requires time, and therefore, the diagnosis requires time.

Further, in view of a burden to the patient, the biopsy can be done only in a limited area and by a limited number of times. Diseased portion may be present at a portion other than the portion identified by the operator. However, such a portion might be overlooked, and as a result, an accurate diagnosis may not be done even if the pathological inspection is performed.

SUMMARY OF THE INVENTION

It is therefore an object of the present invention to provide an improved endoscope system which enables an accurate diagnosis within a relatively short period of time.

For the object, according to the present invention, there is provided an endoscope system provided with a normal light image capturing system, a fluorescent image capturing system and an OCT image capturing system. The normal light image capturing system that captures an image of an object inside a human cavity by illuminating the object with white light. The fluorescent light image capturing system captures an image of the object by illuminating the object with excitation light. The object (i.e., human tissues) emits fluorescent light upon incidence of the excitation light. The OCT image capturing system captures an OCT image of a desired portion of the object. The endoscope system is further provided with a display controlling system that controls a displaying device to display the normal light image, the fluorescent light image and the OCT image simultaneously.

Since the operator can view the three different images simultaneously, an accurate diagnosis can be made within a relatively short period of time.

Optionally, at least one of the normal light image and the fluorescent light image is displayed on the displaying device as an animated image.

Further optionally, an OCT scanning line indicating system may be provided to indicate a line representative of a scanning line corresponding to the OCT image on one of the normal light image and the fluorescent light image, which is displayed as the animated image.

With this configuration, the operator can recognize the positional relationship between the normal or fluorescent image of the object and the tomogram thereof. Thus, accurate observation can be expected.

Optionally, the OCT image may also be displayed as an animated image.

According to another aspect of the invention, there is provided an endoscope system, which is provided with an illuminating optical system that selectively emits, toward an object, visible light and excitation light for exciting the object to fluoresce, an objective optical system that converges light from the surface of the object to form an optical image of the surface of the object, an image capturing system that captures an optical image of a surface of the object and generates an image signal corresponding to the optical image. Further, the endoscope system is provided with a first light guide, a second light guide, an optical coupler for optically coupling the first and second light guides. Furthermore, the endoscope system is provided with a low-coherent light source that emits a low-coherent light beam, the low-coherent light source being provided at a proximal end side of one of the first and second light guides, the light emitted by the low-coherent light source being incident on the one of the first and second light guides, a scanning unit that causes the light beam emerged from the first light guide to scan on a predetermined surface of the object, the scanning unit directing the light beam reflected by the object to the first light guide as a detection light beam, a reflector that reflects a light beam emerged from the second light guide to the second light guide as a reference beam, an optical path length adjusting system that relatively changes a length of an optical path length from the optical coupler to the object via the first light guide and an optical path length from the optical coupler to the reflector via the second light guide, a light detecting device provided at a proximal end side of the other of the first and second light guides, the light detecting device detecting an interfered beam generated due to interference between the reference beam and the detection beam, an OCT image forming system that generates a tomogram based on the signal detected by the light detecting device when the optical path length adjusting system and the scanning unit operate, and a video signal generating system that generates video signals of the optical image of the object and the OCT image based on the image signal output by the image capturing system and the OCT image forming system.

With this configuration, since the video signals corresponding to the image of the surface of the object and the tomogram thereof are output, the image of the surface of the object and the OCT image can be viewed with monitoring the positional relationship therebetween.

Optionally, the endoscope system is provided with a display device that displays the optical image of the surface of the object and the OCT image in accordance with the video signals output by the video signal generating system.

In particular, the image capturing system generates a normal light image signal representing the surface of the object when the illuminating optical system emits the visible light toward the object, the image capturing system generates a fluorescent light image signal representing the surface of the object when the illuminating optical system emits the excitation light toward the object, the OCT image forming system outputs an OCT image signal representing the OCT image of the object, and the video signal generating system generates video signals based on the normal image signals, fluorescent image signals and the OCT image signals, and causes the display device to display the normal light image, the fluorescent light image and the OCT image arranged in a predetermined manner.

Preferably, the video signal generating system includes a memory corresponding to a screen of the display device, the memory storing the normal light image signal, the fluorescent light image signal and the OCT image signal.

In particular, the video signal generating system makes the display device display one of the normal light image and the fluorescent light image as an animated image, and wherein the video signal generating system makes the display device display the OCT image as an animated image.

Optionally, the video signal generating system makes the display device display the other one of the normal light image and the fluorescent light image as a still image.

Preferably, the video signal generating system makes the display device display the normal light image as a color image.

Optionally, the video signal generating system includes a cursor generating system that inserts a cursor indicating a scanning position of the scanning unit in the normal light image or the fluorescent light image.

Further optionally, the endoscope system may be provided with a visible light source that emits the visible light, an excitation light source that emits the excitation light, and a light source switching system that selectively causes the visible light and the excitation light to impinge on the illuminating optical system.

Optionally, the optical path length adjusting system moves the reflector toward/away from a tip of the second light guide to vary the optical path length from the optical coupler to the reflector via the second light guide relative to the optical path length from the optical coupler to the object via the first light guide.

In a particular case, the low-coherent light source may include a super-luminous diode.

DESCRIPTION OF THE ACCOMPANYING DRAWINGS

FIG. 1 is a block diagram schematically illustrating an electrical structure of an endoscope system according to a first embodiment of the invention;

FIG. 2 schematically shows a structure of the tip portion of the endoscope;

FIG. 3 schematically shows a perspective view of the tip portion of the endoscope;

Figure 15:
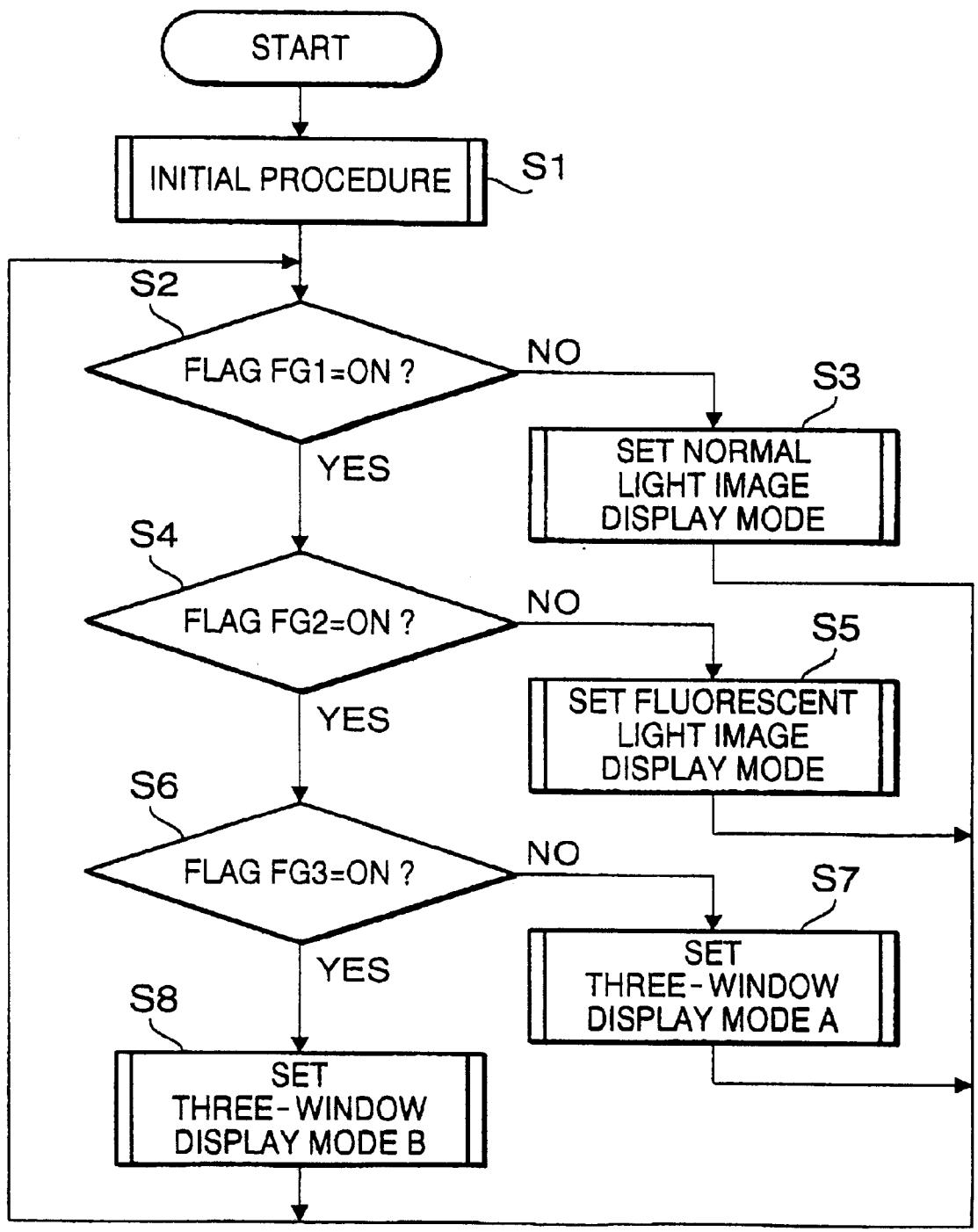

FIGS. 6A through 6J constitute a timing chart corresponding to a normal image display mode;

FIGS. 7A through 7J constitute a timing chart corresponding to a normal image display mode;

FIGS. 8A through 8J constitute a timing chart corresponding to a fluorescent image display mode;

FIGS. 9A through 9J constitute a timing chart corresponding to a fluorescent image display mode;

FIGS. 10A through 10J constitute a timing chart corresponding to a three-window display mode A;

FIGS. 11A through 11J constitute a timing chart corresponding to a three-window display mode A;

FIGS. 12A through 12J constitute a timing chart corresponding to a three-window display modes A and B;

FIGS. 13A through 13J constitute a timing chart corresponding to a three-window display mode B;

FIGS. 14A through 14J constitute a timing chart corresponding to a three-window display mode B; and FIG. 15 shows a flowchart illustrating a display mode switching procedure.

DESCRIPTION OF THE EMBODIMENT

Hereinafter, an embodiment according to the present invention will be described with reference to the accompanying drawings.

Figure 1:
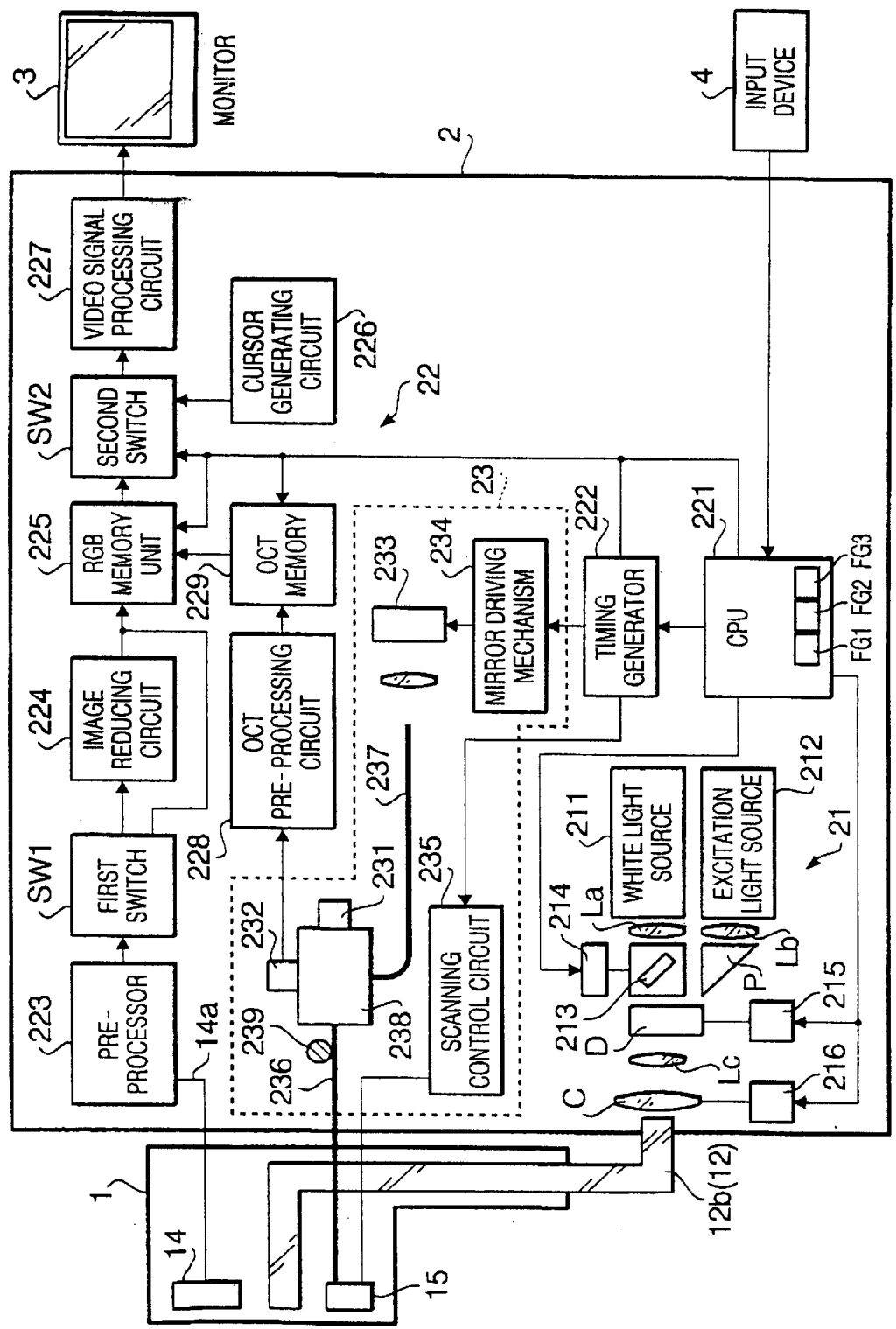

FIG. 1 is a block diagram illustrating an electronic structure of the endoscope system 1000 according to an embodiment of the invention.

As shown in FIG. 1, the endoscope system 11000 includes an endoscope 1, an external device 2 connected to the endoscope 1, a monitor 3 connected to the external device 2, and an input device 4.

Figure 2:
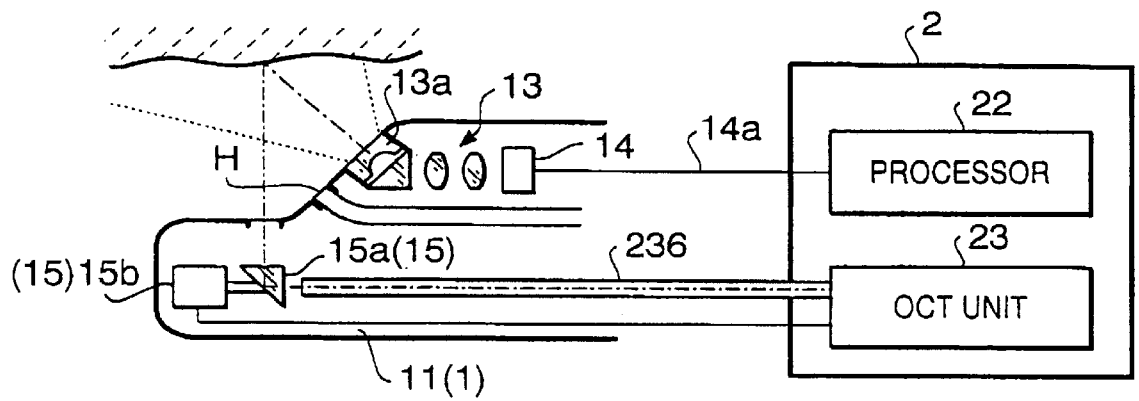

The endoscope 1 includes an insertion tube 11 (see FIGS. 2 and 3), and an operation unit (not shown) is connected to a proximal end of the insertion tube 11. Various operation switches are provided on the operation unit. FIG. 2 schematically shows a structure of the tip portion (i.e., a distal end portion) of the insertion tube 11, and FIG. 3 schematically shows a perspective view of the tip portion of the insertion tube 11.

Figure 3:
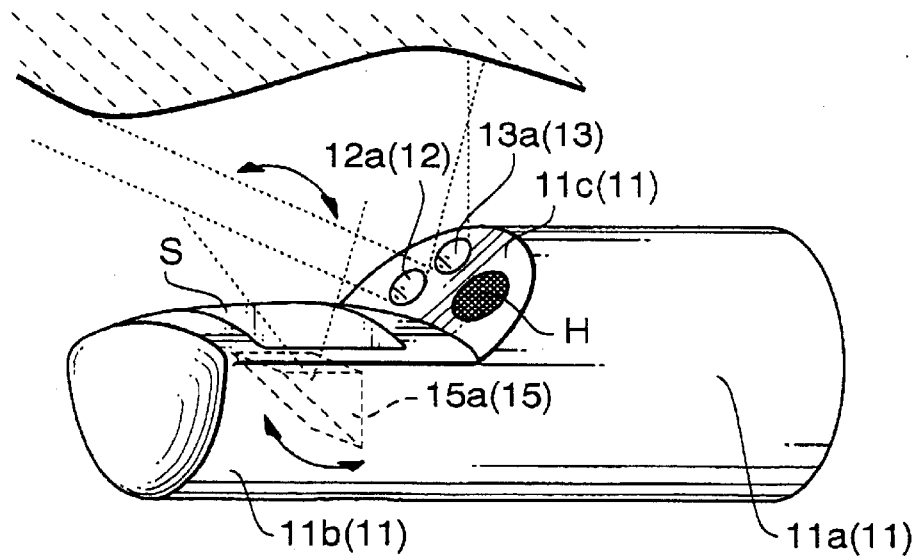

As shown in FIG. 3, the insertion tube 11 includes a cylindrical portion 11a, which is protruded from the proximal end of the endoscope 1, and a flattened portion 11b having a substantially elliptical cross section provided at the tip end of the cylindrical portion 11a. The flattened portion 11b protrudes from the cylindrical portion 11a, and between the cylindrical portion 11a and the flattened portion 11b, a slope portion 11c is formed. On the slope portion 11c, at least three through holes are formed. One of the holes is used as an instrument opening H, and to the other two holes, an illuminating lens 12a for illuminating an object, and an objective lens 13a for observation are tight-fitted, respectively. On the flattened portion 11b, a scanning window S. is formed for an OCT scanning, which will be described later.

Inside the insertion tube 11, an illuminating optical system 12, an objective optical system 13, a CCD (Charge Coupled Device) 14, and an OCT scanning system 15 are arranged.

The illuminating optical system 12 is provided with the Illumination lens 12a and a light guide fiber bundle 12b (hereinafter referred to as a light guide) as shown on FIG. 1. The light guide 12b is inserted through the endoscope 1 and connected to the external device 2 at the proximal end side thereof. The tip end of the light guide 12b faces the illumination lens 12a.

An objective optical system 13 is provided with the objective lens 13a, a cut-off filter, which shields a UV component of the incident light, a prism and a plurality of lenses. The objective optical system 13 converges the incident light on the image receiving surface of the CCD 14 and forms an object image thereon. The CCD 14 outputs an image signal corresponding to the optical image formed on the image receiving surface thereof. The CCD 14 is connected to the external device 2 through a signal line 14a, and the image signal is transmitted to the external device 2.

The OCT scanning unit 15 faces a tip end of an optical fiber 236, which will be described later. The light emerged from the optical fiber 236 is deflected, by a scanning prism 15a, to the scanning window S. The scanning prism 15a is rotated reciprocally about the axis of the optical fiber 236 with a predetermined angular range by a rotation driving unit 15b.

The endoscope 1 constructed as above is connected to the external device 2. The external device 2 will be described in detail hereinafter.

As shown in FIG. 1, the external device 2 is provided with a light source unit 21, a processor 22 and an OCT unit 23.

The light source unit 21 includes a white light source 211, which emits so-called white light, and a UV light source 212, which emits UV light. The UV light is used as an excitation light for exciting the human tissues to fluoresce. The wavelength of the excitation light is approximately 350 nm through 400 nm, and the wavelength of fluorescent light, which is emitted from the human tissues upon incidence of the excitation light, is approximately 420 nm through 600 nm.

On an optical path of the white light emitted by the white light source 211, a collimating lens La, a switching mirror 213, an aperture stop D, a condenser lens Lc, and a rotating filter C are arranged in this order. The switching mirror 213 is connected to a light source switching mechanism 214. Specifically, the light source switching mechanism 214 locates the switching mirror 213 at a retracted position, at which the switching mirror 213 is retracted from the optical path of the white light, or an operable position at which the switching mirror 213 shields the white light (i.e., the switching mirror 213 prevents the white light from proceeding to the aperture stop D).

The aperture stop D is connected to the aperture control mechanism 215. The aperture stop D is controlled by the aperture control mechanism 215 to change the aperture size so as to change the amount of light passed therethrough. The rotatable filter C has a disk like appearance and formed with four fan-shaped filters: RGB color filters (three color filters for red, green and blue components); and a transparent filter. The rotatable filter C is connected to the rotatable filter control mechanism 216. The rotatable filter C is driven by the rotatable filter control mechanism 216 to rotate such that the four filters are sequentially inserted in an optical path. The rotatable filter control mechanism 216 is capable of stopping rotation and maintaining the transparent filter inserted in the optical path.

The white light emitted by the white light source 211 is collimated by the collimating lens La. If the switching mirror 213 is located at the retracted position, the white light is directed to the aperture stop D. The white light, light amount of which is adjusted by the aperture stop D, is converged by the condenser lens Lc, and passes through the rotatable filter C. As described above, the rotatable filter C is rotated by the rotatable filter control mechanism 216 to rotate and the four color filters are sequentially inserted in the optical path. Accordingly, the white light is converted into Blue, Green, Red and white light sequentially, and converged on the proximal end surface of the light guide 12b.

On the optical path of the excitation light emitted by the UV light source 212, the collimating lens Lb and a prism P are arranged in this order. The excitation light emitted by the UV light source 212 is collimated by the collimating lens Lb, reflected by the prism P and is directed to the switching mirror 213. If the switching mirror 213 is located at the operative position (as shown in FIG. 1), it reflects the excitation light toward the aperture stop D. The excitation light, whose light amount is adjusted by the aperture stop D, is converged by the condenser lens Lc and is directed to the rotatable filter C. In this case, the rotatable filter control mechanism 216 inserts the transparent filter in the optical path and stops rotating the rotatable filter C. Then, the excitation light passes through the transparent filter of the rotatable filter C and is converged on the proximal end surface of the light guide 12b.

Thus, the retracted and operative positions of the switching mirror 213 will be referred to as a normal image observation condition, in which the white light emitted by the white light source 211 is directed to the aperture stop D, and a fluorescent image observation condition, in which the excitation light emitted by the UV light source 212 is directed to the aperture stop D. The rotatable filter C rotates to sequentially insert the filters in the optical path so that, in the normal image observation condition, the incident white light is converted into blue, green, red and white light sequentially. In the fluorescent image observation condition, the transparent filter is fixedly inserted in the optical path.

Next, the processor 22 will be described. The processor 22 includes a CPU 221 and a timing generator 222. The CPU 221 is connected with the light source switching mechanism 214 and the rotatable filter control mechanism 216 of the light source unit 21, the timing generator 222, and the input device 4. The timing generator 222 generates various reference clock signals. various processing performed by the processor 22 and various operations performed by the OCT unit 23 are executed in accordance with the reference clocks generated by the timing generator 222.

The CPU 221 controls the light source switching mechanism 214 to switch the switching mirror 213 between the normal observation condition and the fluorescent image observation condition, and controls the rotatable filter control mechanism 216 to set the rotatable filter C to the normal image observation condition or the fluorescent image observation condition. Specifically, a switch for selecting the normal image observation and fluorescent image observation is provided on an operation unit of the endoscope 1. The CPU 221 detects the operation status of the selecting switch, controls the light source switching mechanism 214 and the rotatable filter control mechanism 216 so that the switching mirror 213 and the rotatable filter C are set to one of the normal image observation condition and the fluorescent image observation condition selected by the selecting switch. Further, the CPU 221 controls the aperture control mechanism 215, based on a signal transmitted from an RGB memory unit 225, which will be described later, to adjust the aperture size of the aperture stop D.

The CPU 221, on the other hand, controls the operations executed by the processor 22 and the operations executed by the OCT unit 23 via the timing generator 222.

Further, the processor 22 is provided with a pre-processor 223, a first switch SW1, an image reducing circuit 224, the RGB memory unit 225, a second switch SW2, a cursor generating circuit 226 and a video signal processing circuit 227. It should be noted that, in FIG. 1, the RGB memory unit 225 and the second switch SW2, and a signal line connecting the CPU 221 and the timing generator 222 is shown. Although not shown in FIG. 1, the pre-processor 223, the first switch SW1 and the video signal processing circuit 227 are also connected to the CPU 221 and the timing generator 222, through connecting lines (not shown).

The pre-processor 223 is connected to the CCD 14 through the signal line 14a and the RGB memory unit 225, and capable of receiving the signal from the CCD 14 at a predetermined timing and holding the received signal.

When the switching mirror 213 and the rotatable filter C are set to the normal image observation condition, the Blue light, Green light, Red light and White light are sequentially emitted from the illumination lens 12a at a predetermined timing. The pre-processor 223 receives the signal from the CCD 14 at a predetermined timing and holds the received signals. That is, when the Blue light is emitted, the pre-processor 223 holds the image signal for one frame of image corresponding to the blue light, which is formed on the image receiving surface of the CCD 14. Similarly, when the Green light is emitted, the pre-processor 223 holds the image signal for another frame of image corresponding to the green light, and when the Red light is emitted, the pre-processor 223 holds another image signal for one frame of image corresponding to the red image. It should be noted that, the signal output by the CCD 14 when the white light is emitted by the illumination lens 12a is not held and abandoned.

The pre-processor 223 processes the image signals, for one frame of image, transmitted from the CCD 14, by applying amplification, adjustment of the white balance, gamma correction, and A/D (analog-to-digital) conversion to generate a normal image signal. The processed signals when the object is illuminated with the Blue light, Green light and Red light, respectively, are sequentially transmitted to the first switch SW1. The transmission of the normal image signal is performed such that a set (corresponding to one frame of image of the CCD 14) of signals are transmitted within $1/30$ seconds, and the transmission is repeated.

When the switching mirror 213 and the rotatable filter C are set to the fluorescent image observation setting, the excitation light is emitted from the illumination lens 12a. In this case, the pre-processor 223 retains the image signal transmitted by the CCD 14. Then, the pre-processor 223 processes the retained image signal, i.e., applies the amplification, adjustment of the white balance, the gamma correction, and the A/D conversion to the retained image signal, and transmits the processed signal to the first switch SW1 as the fluorescent image signal. The transmission of the fluorescent image signal is performed once in $1/30$ seconds (corresponding to one frame of image of the CCD 14), and the transmission is repeated.

The first switch SW1 is set to, by the CPU 221, be in a first condition where the signal transmitted from the pre-processor 223 (i.e., the normal image signal or the fluorescent image signal) directly transmitted to the RGB memory unit, or in a second condition where the image signal is transmitted (via not shown signal line) to the image reducing circuit 224. The image reducing circuit 224 converts the received signal to a signal representing a reduced image, and then transmits the converted signal, which corresponds to the reduced image, to the RGB memory unit 225.

The RGB memory unit 225 includes B memory, G memory and R memory (not shown). Each of the B memory, G memory and R memory has a storage capable of storing image data corresponding to a frame of image of the CCD 14. The B memory, G memory and R memory are assigned with predetermined addresses.

The RGB memory unit 225 is connected to the timing generator 222, and capable of storing the received signal at a predetermined timing. Further, the RGB memory unit 225 transmits the stored signal to the second switch SW2 at a predetermined timing. The second switch SW2 is connected to the timing generator 222, and selects the signal transmitted from the RGB memory unit 225 or the signal transmitted from the cursor generating circuit 226 at a predetermined timing, and transmits the selected signal to the video signal processing circuit 227.

The cursor generating circuit 226 generates a signal representative of a bright white line (cursor) on the monitor 3. The signal output by the cursor generating circuit 226 is processed by the video signal processing circuit 227, and the cursor is displayed on the monitor as a white line.

The video signal processing circuit 227 is connected to the monitor 3, and applies a D/A conversion and encoding for a TV system to the signal transmitted from the second switch SW2. In the embodiment, the signal transmitted from the video processing circuit 227 to the monitor 3 is the NTSC signal. It should be noted, the invention is not limited to this method, and any other system, e.g., PAL system can be optionally or alternatively employed.

The processor 22 includes an OCT preprocessing circuit 228 connected to the OCT unit 23, and an OCT memory 229 connected to the OCT preprocessing circuit 228, the RGB memory unit 225 and the timing generator 222. The OCT preprocessing circuit 228 processes the signal transmitted from the OCT unit 23, applies the A/D conversion, and transmits the processed signal as the OCT image signal to the OCT memory 229. The OCT memory. 229 receives the OCT image signal and stores the same. The OCT image signal stored in the OCT memory 229 is transmitted to the RGB memory unit 225 at a predetermined timing.

The above described image reducing circuit 224, the RGB memory unit 225, the OCT memory 229 and the video signal processing circuit 227 function as a video signal generating system. That is, the image reducing circuit 224, the RGB memory unit 225, the OCT memory 229 and the video signal processing circuit 227 edit the normal light image, the fluorescent light image and the OCT image in accordance with the selected image display mode, and display the images on the monitor 3.

The CPU 221 is provided with a register for storing the image display modes. In the register, first through third flags (one-bit flag) FG1, FG2 and FG3 are stored, and a currently selected image display mode is memorized by setting the flags.

On the operation unit of the endoscope 1, an image display mode switching button (not shown) is provided. The button is connected to the CPU 221 through a not shown circuit and, upon operation of the button, the flags FG1, FG2 and FG3 are updated. The CPU 221 detects the currently selected display mode with reference to the values of the flags FG1, FG2 and FG3.

Hereinafter, the OCT unit 23 will be described in detail.

Figure 4:
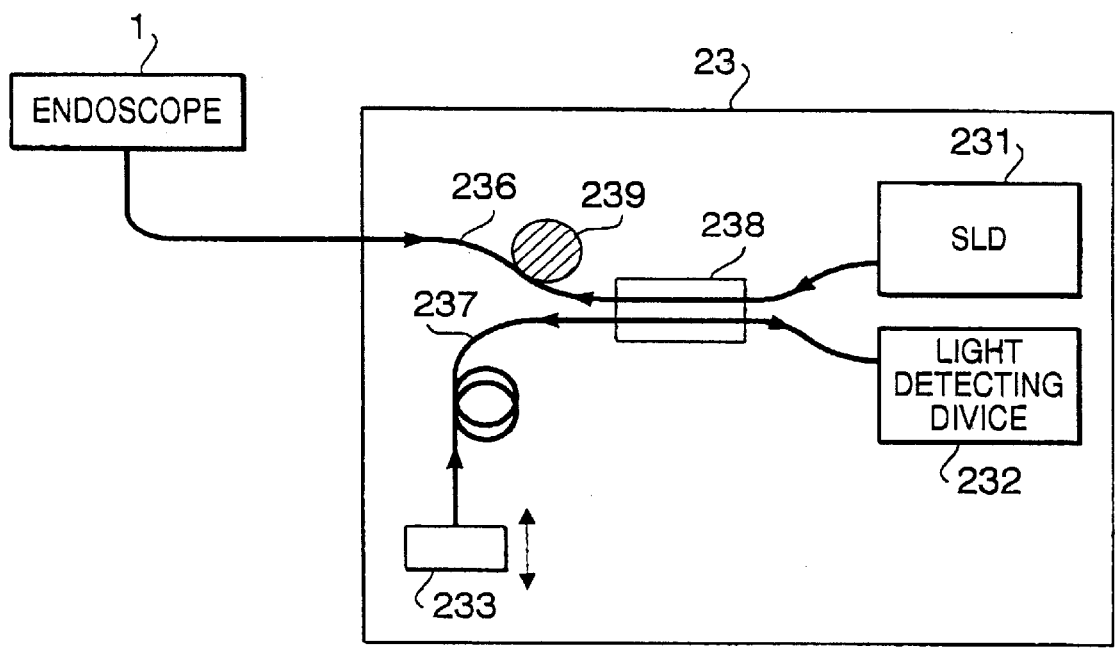
FIG. 4 shows optical paths of the OCT unit.

FIG. 4 shows the optical path of the OCT unit 23. The OCT unit 23 is used for capturing OCT images of the paries of the human cavity. The OCT unit 23 includes a super-luminescent diode (SLD) 231, a light detecting device 232, a reference mirror 233, a mirror driving mechanism 234 and a scanning control circuit 235.

The SLD 231 is a light source emitting a low-coherent light beam at a near-infrared range. The coherent distance of the light beam emitted by the SLD 231 is very short, e.g., in the order of 10 $\mu$m through 1000 $\mu$m. The light detecting device 232 is connected to the OCT pre-processing circuit 228 of the processor 22.

The mirror driving mechanism 234 is for moving the reference mirror 233 at a high speed. The mirror driving mechanism 234 is connected to the timing generator 222 in the processor 22. The scanning control circuit 235 is connected a rotation driving unit 15$b$ of the OCT scanning unit 15 of the endoscope 1, and to the timing generator 222.

Further, the OCT 23 includes a first optical fiber 236, a second optical fiber 237, an optical coupler 238, and a piezo modulating element 239. Each of the optical fibers 236 and 237 is a single mode optical fiber.

The first optical fiber 236 is arranged such that the proximal end thereof faces the SLD 231. The first optical fiber 236 is inserted through the endoscope 1 and the tip end thereof faces the OCT scanning unit 15. The second optical fiber 237 is arranged such that the proximal end thereof faces the photo detector 232. The tip end of the second optical fiber 237 faces the reference mirror 233. It should be noted that the reference mirror 233 is constructed to reciprocate along the axis of the second optical fiber 237.

The optical fibers 236 and 237 are optically coupled using the optical coupler 238. An optical distance, in the first optical fiber 236, from the optical coupler 238 to the tip end thereof, is the same as the optical distance, in the second optical fiber 237, from the optical coupler 238 to the tip end thereof. Further, the first optical fiber 236 is wound around the piezo modulation element 239 having a cylindrical shape, at a portion between the optical coupler 238 to the tip end thereof. The piezo modulation element 239 expands and shrinks in the radial direction at high speed so that the frequency and phase of the light passing through the optical fiber 236 is modulated.

It should be noted that the SLD 231, the light detecting device 232, the reference mirror 233, the optical fibers 236 and 237, and the optical coupler 238 are arranged as described above to form the Michelson interferometer.

The OCT unit 23 is capable of capturing OCT images of an object (e.g., paries of the human cavity), with the scanning window S of the tip end portion of the insertion tube 11 facing the object.

The low-coherent light emitted by the SLD 231 is incident on the first optical fiber 236, and is split by the optical coupler 238 into the light proceeds along the first optical fiber 236 to the tip end thereof, and into the light proceeds along the second optical fiber 237 to the tip end thereof. The light guided by the first optical fiber 236 is deflected by the scanning prism 15$a$ of the OCT scanning unit 15 of the endoscope 1, and emerged therefrom as a scanning light beam. The scanning light beam emerged from the scanning window S is reflected by various tissues on and inside the paries of the human cavity. The reflected light beam enters the endoscope 1 through the scanning window S, and is directed to the optical coupler 238, through the scanning prism 15$a$, by the first optical fiber 236.

The light beam directed by the second optical fiber 237 is emerged from its tip end and reflected by the reference mirror 233. The light beam reflected by the reference mirror 233 is incident on the second optical fiber 237 again, and proceeds toward the optical coupler 238 as a reference light beam.

The detection light beam transmitted through the first optical fiber 236 and the reference light beam transmitted through the second optical fiber 237 interfere at the optical coupler 238. It should be noted, however, that the detection beam is a beam reflected by each layer of the biotissues forming the body cavity, it reaches the optical coupler with some delays.

On the other hand, the reference beam is reflected by the reference mirror 233, and therefore, reaches the optical coupler 238 at a fixed timing. Accordingly, from among the various detection beams reflected at various layers of the biotissues, only a beam traveled along an optical path whose length is the same as the optical length of the beam which proceeds from the optical coupler 238 to the reference mirror 233 through the second optical fiber 237 and then returns therefrom to the optical coupler 238. Thus, from among the detection beams, one which is reflected by a certain one of the layers beneath the paries interferes with the reference light beam.

The interfering beams proceed from the optical coupler 238 through the second optical fiber 237, and detected by the light detecting device 232. If the mirror driving mechanism 234 changes a position of the reference mirror 233 along the axis of the second optical fiber 237, the optical path length of the reference light beam changes. In such a case, a detection beam interferes with the reference beam changes, i.e., a layer subjected to detection changes. In other words, a depth beneath the paries subjected to detection changes.

The scanning control circuit 235 and the mirror drive mechanism 234 operate synchronously with the clock signals transmitted from the timing generator 222. Specifically, the scanning control circuit 235 drives the rotation drive unit 15$b$ of the OCT scanning unit 15 to reciprocally rotate the scanning prism 15$a$ within a predetermined angular range. Then, the light beam emerged from the scanning prism 15$a$ impinges on the paries, the illuminating position being moved along a predetermined line segment (i.e., an OCT scanning line). In this case, at every predetermined interval, during which the impinging beam is regarded as to be located at the same position, the mirror driving mechanism 234 reciprocates the reference mirror 233 at a high speed.

Thus, on a plurality of points on the OCT scanning line mutually formed on the paries, scanning is performed in the depth direction. Depending on the condition of the biotissues beneath the paries, distribution of intensity of light varies. Thus, depending on the distribution of intensity of light, from the position within a range between the surface of the paries and a layer at a predetermined depth therefrom, tomogram can be obtained.

As described above, the light detecting device 232 outputs the interfering light beams as an electrical signal, and light beams which do not interfere with the reference light as a noise. If an signal-to-noise (S/N) ratio is relatively low, an accurate signal detection cannot be performed. Therefore, in order to raise the SIN ratio, a so-called heterodyne detection method is utilized. That is, the light beam passing through the first optical fiber 236 is modified, by the piezo modulating element 239, in terms of its frequency and phase. As a result of this modification, the frequency and the phase of the detection light beam slightly shifts with respect to those of the reference light beam. Therefore, the interfered light includes beat. When the light detection device 232 receives the interfered light including the beat, it outputs a beat signal.

The pre-processing circuit 228 of the processor 22 demodulate the beat signal output by the light detection device 232 to derive the signal component accurately. The demodulated signal is A/D (analog-to-digital) converted by the pre-processing circuit 228 and stored in the OCT memory 229. The OCT memory 229 retrieves the stored data at a predetermined timing, and transmit the same to the RGB memory unit 225 as an OCT image signal.

Procedure for writing data in the RGB memory unit 225 will be described.

The CPU 221 is capable of transmitting writing allowing signals respectively allowing data writing in R, G and B memories, via the timing generator 225, to the RGB memory unit 225. The RGB memory unit 225 operates such that data can be written in the R, G and B memories when the writing allowing signals for the R, G and B memories are received, respectively. That is, when The RGB memory unit 225 receives the writing allowing signal for the B memory together with the image signal, the RGB memory unit 225 stores the received image signal in the B memory. Similarly, when The RGB memory unit 225 receives the writing allowing signal for the G memory together with the image signal, the RGB memory unit 225 stores the received image signal in the G memory, and when The RGB memory unit 225 receives the writing allowing signal for the R memory together with the image signal, the RGB memory unit 225 stores the received image signal in the R memory.

The RGB memory unit 225 is provided with a register that stores the addresses of R, G and B memories at which data is to be stored. The CPU 221 transmits address count enabling signals to the R, G and B memories of the RGB memory unit 225, respectively, via the timing generator 222. In each of the R, G and B memories, the address at which the received data is to be stored is incremented upon receipt of the address count enabling signal for the each of the R, G and B memories.

The RGB memory unit 225 increments the count of the address in the registers when the address count enabling signals for the R, G and B memories are being received, respectively. That is, the RGB memory unit 225 increments the address of the B memory, to which data is to be stored, when it receives the B memory address count enabling signal. Similarly, the RGB memory unit 225 increments the address of the G memory, to which data is to be stored, when it receives the G memory address count enabling signal, and the RGB memory unit 225 increments the address of the R memory, to which data is to be stored, when it receives the R memory address count enabling signal.

The CPU 221 controls data writing in the RGB memory unit 225 by controlling the light source switching mechanism 214, the rotatable filter control mechanism 216, so that the four display modes are realized. That is, the images are displayed on the monitor 3 in accordance with the selected on of the four display modes.

Figure 5A:
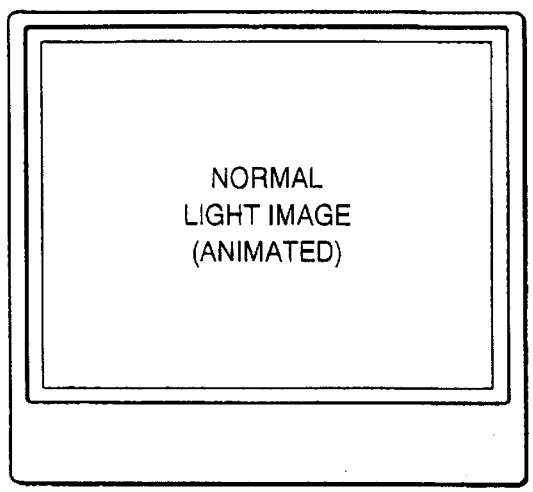
FIGS. 5A through 5D show screen images for various displaying modes.
Figure 5B:
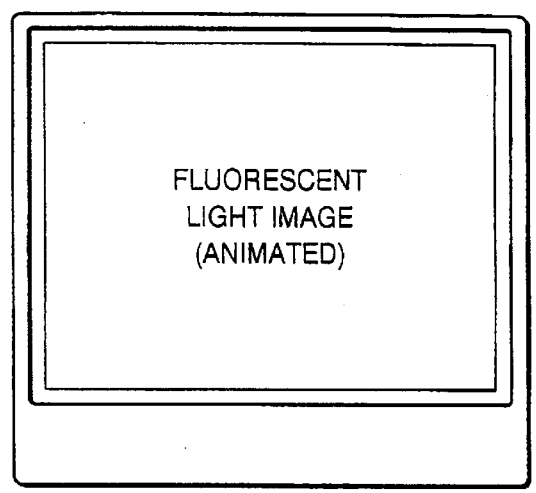
Figure 5C:
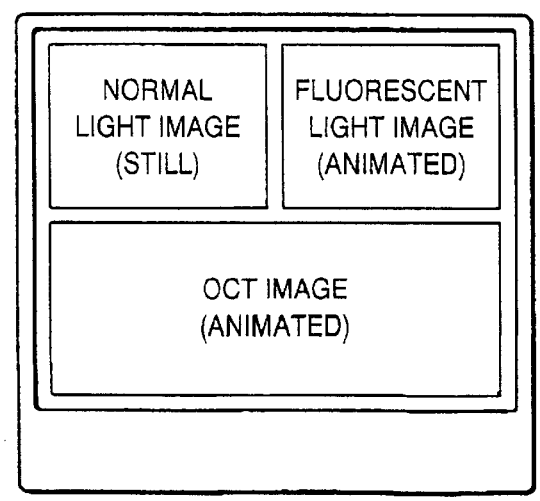
Figure 5D:
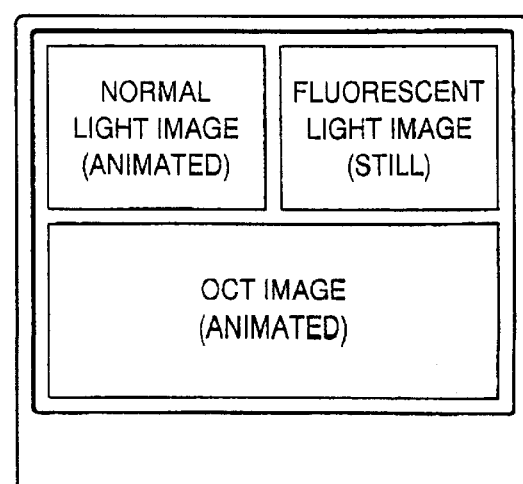

FIGS. 5A through 5D show screen images in various display modes. Specifically, FIG. 5A shows a screen image in the normal light image (animated image) display mode, FIG. 5B shows a screen image in the fluorescent image display mode, FIG. 5C shows a three-window mode A in which the normal light image (still), the fluorescent light mage (animated), and the OCT image (animated) are displayed simultaneously, and FIG. 5D shows a three-window mode B in which the normal light image (animated), the fluorescent light mage (still), and the OCT image (animated) are displayed simultaneously.

In the three-window modes A and B, the screen is divided into upper and lower windows, and the upper window is divided into right and left windows. That is, the upper left, the upper right, and the lower windows are displayed on the screen of the monitor 3. The upper left window shows the normal light image, the upper right window shows the fluorescent light image, and the lower window shows the OCT image. In the three-window mode A, the upper left window shows the normal light image as a still image, and the upper right window shows the fluorescent light image as an animated image. In the three-window mode B, the upper left window shows the normal light image as an animated image, and the upper right window shows the fluorescent light image as a still image. In mode A and mode B, the OCT image is shown as an animated image.

Each display mode will be described in detail with reference to the timing charts shown in FIGS. 6A–14J. The time charts show data writing procedures in the RGB memory unit 225 of the processor 22. The data writing procedures are different for respective display modes.

It should be noted that the monitor 3 in the embodiment is adhered to the NTSC (National Television Standards Committee) system, and the processor 22 transmits the NTSC TV signal to the monitor 3. According to the NTSC system, a frame of an image is updated at every $\frac{1}{30}$ seconds. One frame of image consists of two fields (odd and even fields) which are alternately updated at $\frac{1}{60}$ seconds synchronously with a vertical synchronizing signal which is generated at every $\frac{1}{60}$ seconds.

Scanning in each of the odd and even fields is performed synchronously with a horizontal synchronizing signal. That is, at each occurrence of the horizontal synchronizing signal, one scanning line is drawn on the screen of the monitor 3.

The timing generator 222 generates the horizontal and vertical synchronizing signals, synchronously with which an image is formed on the screen of the monitor 3. Further, data storing procedure in the RGB memory unit 225 is also performed with reference to the horizontal and vertical synchronizing signals. Hereinafter, data storing procedure for each display mode will be described.

Normal Image Display Mode

FIGS. 6A–6J show a timing chart corresponding to the normal image display mode with a scale of the horizontal synchronizing signal. FIGS. 7A–7J show a timing chart corresponding to the normal image display mode with a scale of the vertical synchronizing signal. The vertical synchronizing signal is generated at every $\frac{1}{60}$ seconds, FIGS. 7A–7J show the chart for two periods (i.e., $\frac{1}{30}$ seconds). Within 1/30 seconds, the pre-processor 223 outputs the image signals for one frame of image corresponding to B, G and R light, sequentially.

In the normal image display mode, the first switch SW1 directly connects the pre-processor 223 with the RGB memory unit 225 (without the image reduction circuit 224 interposed). The second switch SW2 is set such that the output signal of the RGB memory unit 225 is always transmitted to the video signal processing circuit 227. The switching mirror 213 and the rotatable filter C are set in the normal image observation condition. Thus, from the illumination lens 12a of the illumination optical system 12, the B, G, R and white light are sequentially emerged.

The pre-processor 223 sequentially receives the image signal for one frame when the B light is emitted, G light is emitted and the R light is emitted, and holds the received signals. As afore-mentioned, the signal when the white light is emitted is not used and therefore is not held. Based on the received signals, the pre-processor 223 generates the normal light image signal corresponding to the B light, G light and R light, respectively. The normal light image signals thus generated are sequentially transmitted through the first switch SW1 to the RGB memory unit 225.

It should be noted that the pre-processor 223 transmits the signal corresponding to two lines of the CCD 14 within one horizontal scanning period. FIGS. 6A–6J show a case where the pre-processor 223 transmits the normal light image signal corresponding to the B light for two horizontal scanning periods.

At this stage, in the RGB memory unit 225, the B memory writing allowing signal is ON. Therefore, the normal light image signal is stored in the B memory. When the B memory writing allowing signal is ON, the B memory address count enabling signal is ON. Therefore, the RGB memory unit 225 writes the normal light image signal in the B memory with incrementing the subjected address of the B memory. While the data is stored in the B memory, the G memory writing allowing signal and the R memory writing allowing signal are OFF, and therefore no data is written in the G memory or R memory.

The condition shown in FIGS. 6A–6J continues and the RGB memory unit 225 stores the image data corresponding to a frame of image of the CCD 14. Then, the pre-processor 223 starts transmitting the normal light image signal corresponding to the G light. Then, the RGB memory unit 225 stores the image data corresponding to a frame of image corresponding to the G light. At this stage, in the RGB memory unit 225, the G memory writing allowing signal is ON. Therefore, the normal light image signal is stored in the G memory. When the G memory writing allowing signal is ON, the G memory address count enabling signal is ON. Therefore, the RGB memory unit 225 writes the normal light image signal in the G memory with incrementing the subjected address of the G memory. While the data is stored in the G memory, the B memory writing allowing signal and the R memory writing allowing signal are OFF, and therefore no data is written in the B memory or R memory.

When the image data corresponding to the G light has been stored, the similar procedure is performed with respect to the R light, and the image data is stored in the R memory.

As shown in FIGS. 7A–7J, the series of data storing procedure in the B memory, G memory and the R memory is performed once in 1/30 seconds, and is repeated at every 1/30 seconds. Thus, the data in the RGB memory unit 225 is updated at every 1/30 seconds. The video signal processing circuit 227 retrieves the data stored in the RGB memory unit 225, applies the D/A conversion, encoding in accordance with the NTSC system, and transmits the resultant signals to the monitor 3. Then, the normal light image is displayed on the entire area of the screen of the monitor 3 as shown in FIG. 5A.

Fluorescent Image Display Mode

FIGS. 8A–8J show a timing chart corresponding to the fluorescent image display mode with a scale of the horizontal synchronizing signal. FIGS. 9A–9J show a timing chart corresponding to the fluorescent image display mode with a scale of the vertical synchronizing signal.

In the fluorescent image display mode, the first and second switches are set similarly to the normal image display mode. The switching mirror 213 and the rotatable filter C are set to the fluorescent image observing condition.

From the illumination lens 12a, the excitation light is emerged towards the paries, which emits the fluorescent light. The fluorescent light emitted by the paries and the excitation reflected by the paries is directed to the objective optical system 13. The objective optical system 13 shields the excitation light component from the incident light, and converges the light on the image receiving surface of the CCD 14 so that the fluorescent light image is formed thereon. The CCD 14 converts the received image into the image signal, and transmits the same to the pre-processor 223.

The pre-processor 223 receives and holds the signal corresponding to one frame of the CCD 14, and generates the fluorescent image signal. Then, the pre-processor 223 transmits the fluorescent image signal to the RGB memory unit 225 via the first switch SW1.

The pre-processor 223 transmits two lines of image signal within on horizontal scanning period. In FIGS. 8A–8J, a condition where the signals corresponding to the two scanning lines is shown.

At this stage, in the RGB memory unit 225, all of the B memory writing allowing signal, G memory writing allowing signal, R memory writing allowing signal, B memory address count enabling signal, G memory address count enabling signal and R memory address count enabling signal are ON. Therefore, the RGB memory unit 225 stores the received signal in the B memory, G memory and R memory, at the same time, with counting the address.

The data writing procedure, for one frame of image, in the RGB memory unit 225 is performed once in 1/30 seconds. Thus, the data stored in the RGB memory unit 225 is updated once in 1/30 seconds. The video signal processing circuit 227 retrieves the data stored in the RGB memory unit 225, applies the D/A conversion, encoding in accordance with the NTSC system, and transmits the resultant signal to the monitor 3. The monitor 3 receives the signal, and displays the fluorescent image on the entire area of the screen of the monitor 3 as shown in FIG. 5B. It should be noted that, since the same data is stored in the B memory, G memory and R memory of the RGB memory unit 225, the image displayed on the monitor 3 is a monochrome image.

Three-window Mode A

The three-window mode A is a mode in which the fluorescent image is displayed in the upper right area of the screen of the monitor 3 as an animated image, and the OCT image is displayed in the lower area of the screen of the monitor 3 as an animated image. In the upper left area of the screen of the monitor 3, the normal light image is displayed as a still image.

FIGS. 10A–10J show a timing chart corresponding to the upper window of the three-window mode A with a scale of the horizontal synchronizing signal. FIGS. 11A–11J show a timing chart corresponding to the three-window mode A with a scale of the vertical synchronizing signal.

It should be noted that, for the lower area of the screen of the monitor 3, the similar procedure is performed in the three-window mode A and the three-window mode B. FIGS. 12A–12J show a timing chart corresponding to the lower window of the three-window mode A (or B) with a scale of the horizontal synchronizing signal.

In the three-window mode A, the first switch SW1 is set such that the data transmitted from the pre-processor 223 is transmitted to the image reduction circuit 224. Further, the second switch SW2 is set such that the signal transmitted from the RGB memory unit 225 and the signal transmitted from the cursor generating circuit 226 are switched at a predetermined timing and transmitted to the video signal processing circuit 227. The switching mirror 213 and the rotatable filter C are set to the fluorescent image observation condition.

From the pre-processor 223, the fluorescent image signal is transmitted as in the fluorescent image mode. The first switch SW1 receives the fluorescent image signal from the pre-processor 223 and transmits the same to the image reduction circuit 224. The image reduction circuit 224 converts the received signal such that the image size of the received signal is reduced to ¼ thereof (½ in either vertical or horizontal direction). Then, the image reducing circuit 224 converts the received image signal so as to correspond to the upper right area of the screen of the monitor 3, and transmits the converted signal to the RGB memory unit 225.

As shown in FIGS. 10A and 10C, the RGB memory unit 225 receives the fluorescent image signal corresponding to two scanning lines within one horizontally scanning period (between two successive horizontally synchronizing signals). It should be noted that, as afore-mentioned, the fluorescent image signal has been converted by the image reduction circuit 224, and therefore only contains data corresponding to the right half of a scanning line.

The B memory address count enabling signal, G memory address count enabling signal, and R memory address count enabling signal are ON for one entire scanning line. When each address count enabling signal is ON and a period corresponding to a half of one scanning line has passed, the B memory write allowing signal, G memory write allowing signal and R memory write allowing signal are ON. When each write allowing signal is ON, the RGB memory unit 225 writes the fluorescent image signal in the B memory, G memory and R memory.

As shown in FIGS. 11A–11J, the fluorescent image signal is transmitted to the RGB memory unit 225 only in a period corresponding to the upper half of the screen of the monitor 3, and is not transmitted within a period corresponding to the lower half of the screen of the monitor 3. The B memory writing allowing signal, G memory writing allowing signal, and R memory writing allowing signal are ON only when the fluorescent image signal is transmitted. The B memory address count enabling signal, G memory address count enabling signal and R memory address count enabling signal are turned ON when the fluorescent image signal is transmitted, and kept ON after the transmission of the fluorescent image signal is finished. Thus, the memory address count enabling signals are ON even in a period corresponding to the lower half of the screen of the monitor 3. In other words, the memory address count enabling signals are ON during a period corresponding to one frame of image.

According to the procedure described above, in the RGB memory unit 225, at an area corresponding to the upper right area of the screen of the monitor 3, the image signal of the fluorescent image is stored. In the areas of the RGB memory unit 225 corresponding to the upper left and lower areas of the screen of the monitor 3, no image data is stored.

Following the above-described procedure, the OCT image signal will be written. The OCT pre-processor 228 receives the signal output by the OCT unit 23,. and based on the received signal, construct a tomogram, and then generates the OCT image signal. The OCT image signal is transmitted to the OCT memory 229, and then stored therein.

-As shown in FIGS. 11A–11J, in the RGB memory unit 225, a predetermined interval after writing of the image signal corresponding to one frame of fluorescent image was finished, the B, G and R memory address counter enabling signals are turned ON. Within a period corresponding to the upper half area of the screen of the monitor 3, the writing allowing signal for each memory remains OFF.

When the period corresponding to the upper half of the screen has passed, the OCT memory 229 start transmitting the OCT image signal. At the same time, the B, G and R memory writing allowing signals are turned ON. Then, the RGB memory unit 225 stores the OCT image signal in the areas, of the B, G and R memories, corresponding to the lower area of the screen of the monitor 3. When the period corresponding to the lower area of the screen has passed, transmission of the OCT image signal is terminated. At the same time, the memory address count enabling signal, and writing allowing signal for each memory is turned OFF.

With the above procedure, at the area of the RGB memory unit 225 corresponding to the upper right area of the screen, the fluorescent image is written, and at the area of the RGB memory unit 225 corresponding to the lower left area of the screen, the OCT image is written.

One sequence of the above-described data storing in the RGB memory unit 225 is performed in every ⅟30 seconds. Thus, the data stored in the RGB memory unit 225 is updated at every ⅟30 seconds.

The second switch SW2 transmits the data stored in the RGB memory unit 225 to the video signal processing circuit 227. It should be noted, however, when the data corresponding to the central linear portion of the upper right area of the screen is processed, The switch SW2 transmits the data output by the cursor generating circuit 226 to the video signal processing circuit 227, instead of the data stored in the RGB memory unit 225. With this procedure, in the upper right area of the screen, where the fluorescent light image is displayed, a cursor is displayed as a horizontally extending white line. The cursor represents a position of a mutually formed OCT scanning line on the paries.

The video signal processing circuit 227 retrieves the data stored in the RGB memory unit 225, applies the D/A conversion and encoding in accordance with the NTSC system, so as to display the fluorescent light image and the OCT image on the screen of the monitor 3 (i.e., in the three-window mode A), as shown in FIG. 5C. As afore-mentioned, the fluorescent light image is a monochromatic animated image, which is displayed in the upper right area of the screen, and the OCT image is a monochromatic animated image, which is displayed in the lower area of the screen of the monitor 3.

In the above-described procedure, at the area of the RGB memory unit 225 corresponding to the upper left area of the screen of the monitor 3, no data is written. In this area of the screen, the normal light image obtained in advance is displayed as a reduced still image.

Three-window Mode B

In the three-window mode B, the normal light image is displayed in the upper left area of the screen of the monitor 3 as an animated image, and the OCT image is displayed in the lower area of the screen as the animated image.

FIGS. 13A–13J show a timing chart corresponding to the upper windows of the three-window mode B with a scale of the horizontal synchronizing signal. FIGS. 14A–14J show a timing chart corresponding to the three-window mode B with a scale of the vertical synchronizing signal. As aforementioned, for the lower area of the screen, the same procedure is performed in the three-window mode A and in the three-window mode B, as shown in FIGS. 12A–12J.

In the three-window mode B, the first switch SW1 is set such that the data transmitted from the pre-processor 223 is transmitted to the image reduction circuit 224. The second switch SW2 is set such that the data transmitted from the RGB memory unit 225 and the data output by the cursor generating circuit 226 is switched at a predetermined timing and transmitted to the video signal processing circuit 227. The switching mirror 213 and the rotatable filter C are set in the normal light image observation condition.

At this stage, the pre-processor 223 sequentially outputs the normal light image signals corresponding to the B, G and R light, respectively. The first switch SW1 receives the normal light image signals and transmits the same to the image reduction circuit 224. The image reduction circuit 224 converts the received image signals to the signals representing an image corresponding to the upper left area of the screen, and transmits the converted signals to the RGB memory unit 225.

The RGB memory unit 225 receives the normal image signals corresponding to two scanning lines within one horizontal scanning period as shown in FIGS. 13A and 13B. As described above, since the normal image signals have been converted by the image reduction circuit 224, the normal image signals received by the RGB memory unit 225 contain only the left half of each scanning line. In FIGS. 13A–13J, the signals when the normal image signals corresponding to the B light is transmitted to the RGB memory unit 225 are indicated, and therefore, in this timing chart, only the data writing process in the B memory is indicated.

When the data transmission to the RGB memory unit 225 starts, the B memory writing allowing signal, and the B memory address count enabling signal are turned ON simultaneously. Then, the normal image signal is transmitted until a period corresponding to a half of a scanning line has passed. During this period, the RGB memory unit 225 writes the normal light image signal in the B memory in the order of the address. When the period corresponding to the half of the horizontal scanning has passed, the B memory writing allowing signal is turned OFF, and writing the signal in the B memory is terminated. As shown in FIG. 13F, however, the B memory address count enabling signal remains ON until a period corresponding to one horizontal scanning has passed. Therefore, the normal light image signal is written in an area of the RGB memory unit 225 corresponding to the upper left area of the screen.

When this procedure is repeated, as shown in FIGS. 14A–14J, within a period corresponding to the upper half of the screen of the monitor 3, the data writing procedure of the normal light image, with respect to the B light, is performed. In the period corresponding to the lower half of the screen, since only the B memory address count enabling signal is ON, no data is written in the area of the RGB memory unit 225 corresponding to the lower half of the screen.

Further, with a predetermined interval, transmission of the normal light image with respect to the G light starts. At the same time, the B, G and R memory address count enabling signals are turned ON. At this stage, the G memory writing allowing signal is also turned ON. However, the B and R memory writing allowing signals remain OFF. Thus, the normal light image signal is written only in the G memory. It should be noted that the writing of the normal light image in the G memory is performed only for the upper left area of the screen of the monitor 3 as is done when the normal light image signal is written in the B memory.

When a period corresponding to the upper half of the screen has passed, the transmission of the normal light image is terminated. At the same time, transmission of the OCT image signal is initiated, and B and R memory writing allowing signals are turned ON. That is, all the memory writing allowing signals are turned ON when the transmission of the OCT image signal is started. Accordingly, the OCT image signal is simultaneously written in the areas of the R, G and B memories of the RGB memory unit 225 corresponding to the lower half of the screen of the monitor.

When the period corresponding to the lower half of the screen has passed, the transmission of the OCT signal is terminated, and the memory writing allowing signal and the memory address count enabling signal for each memory are turned OFF. Thus, writing of the OCT image signal is terminated.

Further, a predetermined interval has passed, transmission of the normal light image signal with respect to the R light starts. In this case, the R memory writing allowing signal and the R memory address count enabling signal are turned ON. Accordingly, in the R memory of the RGB memory unit 225, the normal light image is written. Similarly to the case where the normal light image signal is written in the B memory and G memory, writing of the normal light image signal in the R memory is done with respect to the upper left area of the screen of the monitor 3.

When a period corresponding to the upper half of the screen has passed, transmission of the normal light image signal is terminated. At the same time, the R memory writing allowing signal is turned OFF. The R memory address count enabling signal remains ON during a period corresponding to the lower half of the screen of the monitor 3. However, no data is stored in the R memory during this period.

As shown in FIGS. 14A–14J, during two vertical synchronizing periods (i.e., 1/30 seconds), in the area of the RGB memory unit 225 corresponding to the upper left area of the screen of the monitor 3, the normal light image signals are written, and in the area of the RGB memory unit 225 corresponding to the lower half of the screen, the OCT image signal is written. Therefore, the data stored in the RGB memory unit 225 is updated at every 1/30 seconds.

The second switch SW2 transmits the data stored in the RGB memory unit 225 to the video signal processing circuit 227. The second switch SW2 transmits the data output by the cursor generating circuit 226 instead of the data from the RGB memory unit 225 when the data corresponding to the central linear part of the upper left area of the screen. With this operation, a horizontally extending cursor (i.e., a line) is displayed within the upper left area of the screen in which the normal light image is displayed. The cursor indicates the position of an OCT scanning line mutually formed on the paries.

The video signal processing circuit 227 retrieves the data stored in the RGB memory unit 225, applies the D/A conversion and encoding in accordance with the NTSC system, and displays the normal light image and the OCT image as animated images (three-window mode B) as shown in FIG. 5D. That is, in the upper left area of the screen, the animated normal light image (color image) is displayed, and in the lower area of the screen, the animated monochromatic OCT image is displayed.

In the above procedure, in the area of the RGB memory unit 225 corresponding to the upper right area of the screen of the monitor 3, no data is written. In the upper right area of the screen, a fluorescent light image obtained in advance is displayed as a reduced still image.

From among the four display modes described above, the operator selects a desired mode. The selection of the display mode will be described.

The processor unit 22 stores three flags: a first flag FG1; a second flag FG2; and a third flag FG3. With the three flags FG1, FG2 and FG3, the currently selected display mode is indicated. The relationship between the ON/OFF condition of the flags and the selected mode is indicated in TABLE I.

TABLE I

| selected mode | FG1 | FG2 | FG3 |
| --- | --- | --- | --- |
| NORMAL | OFF | (OFF) | (OFF) |
| FLUORESCENT | ON | OFF | (OFF) |
| THREE-WINDOW A | ON | ON | OFF |
| THREE-WINDOW B | ON | ON | ON |

It should be noted that, in TABLE I, the status indicated with parentheses does not affect the determination of the display mode, and could be either ON or OFF.

Upon operation of a switch on the operation unit of the endoscope 1, the ON/OFF status of the flags FG1, FG2 and FG3 is changed such that the four display modes are selected sequentially and cyclically. That is, when the normal light image display mode is currently selected and the switch is operated, the fluorescent light image display mode is selected. If the switch is operated when the three-window mode B is currently selected, the normal light image is selected.

The CPU 221 of the processor unit 22 checks the status of the flags FG1, FG2 and FG3 to determine the display mode currently selected. Then, the CPU 221 sets the endoscope system to operate in the selected display mode.

FIG. 15 is a flowchart illustrating the display mode setting procedure, which starts when the operator turns ON the power switch of the endoscope and the white light source 21 and the excitation light. The procedure shown in FIG. 15 is executed by the CPU 221.

In S1, the CPU 221 executes an initial procedure. During the initial procedure, the flags FG1, FG2 and FG3 are set to default status, i.e., OFF status. In S2, the CPU 221 determines whether the first flag FG1 is in ON status. If FG1=OFF (S1: NO), the CPU 221 sets the display mode to the normal light image display mode in S3. If FG1=ON (S1: YES), control proceeds to S4, where the CPU 221 determines whether the second flag FG2 is in ON status. If FG2=OFF (S4: NO), control proceeds to S5, where the display mode is set to the fluorescent image display mode. If FG2=ON (S4: YES), control proceeds to S6 where the CPU 221 determines whether the third flag FG3 is ON. If FG3=OFF (S6: NO), then the display mode is set to the three-window mode A (S7). If FG3=ON (S6: YES), then the display mode is set to the three-window mode B (S8).

Specifically, in S7, firstly, the three-window mode B is once selected. Then, in the upper left area of the screen of the monitor 3, the normal light image is displayed, and in the lower area of the screen, the OCT image is displayed. In the upper right area, no image is displayed. Thereafter, the displayed mode is switched to the three-window mode A. Then, in the upper right area of the screen, the fluorescent light image is displayed as an animated image, and in the lower area of the screen, the OCT image is displayed as the animated image. At this stage, in the area of the RGB memory unit 225 corresponding to the upper left area of the screen no data is newly written. Therefore, in the upper left area of the screen, the still normal light image, which was set when the three-widow mode B was temporarily selected, remains displayed. Accordingly, when the display mode is finally set to the three-window mode A, the operator can simultaneously view the normal light image (still), the fluorescent light image (animated), and the OCT image (animated) within a single screen.

Similarly, in S8, before the three-window mode B is selected, the three-window mode A is temporarily selected. Then, in the upper right area of the screen of the monitor 3, the fluorescent light image is displayed, and in the lower area of the screen, the OCT image is displayed. In the upper left area, no image is displayed. Thereafter, the displayed mode is switched to the three-window mode B. Then, in the upper left area of the screen, the normal light image is displayed as an animated image, and in the lower area of the screen, the OCT image is displayed as the animated image. At this stage, in the area of the RGB memory unit 225 corresponding to the upper right area of the screen no data is newly written. Therefore, in the upper right area of the screen, the still fluorescent light image, which was set when the three-widow mode A was temporarily selected, remains displayed. Accordingly, when the display mode is finally set to the three-window mode B, the operator can simultaneously view the normal light image (animated), the fluorescent light image (still), and the OCT image (animated) within a single screen.

The operation of the endoscope system configured as above will be described. When the operator switches ON the external device 2, the white light source 211 and the excitation light source 212 of the light source unit 21 are turned ON. Then, the CPU 221 starts the procedure shown in FIG. 15.

At this stage, the operator inserts the insertion tube 11 of the endoscope 1 inside the human cavity of a patient, and locates the objective lens 13a of the objective optical system 13 and the scanning window S to face the portion of the paries to be observed. As aforementioned, the display mode is initially set to the normal light image display mode. Accordingly, on the monitor 3, the normal light image of the objective portion of the paries is displayed over the entire screen of the monitor 3. The operator is capable of changing the display mode by operating a switch, as described above.

If the operator selects the three-window mode A, the normal image is displayed as a still image, and the fluorescent light image and the OCT image are displayed as animated images. In the fluorescent light image, a cursor is displayed to indicate the OCT scanning line. By locating the cursor on a portion which might be diseased with monitoring the fluorescent image, the tip of the endoscope 1 can be located at the position suitable for observing the portion which might be diseased. At this stage, the OCT image corresponds to the portion where the cursor is located in the fluorescent light image. As above, the operator can move the tip of the endoscope 1 with monitoring the animated fluorescent light image, and can observe the OCT image at a desired position. It should be noted that the operator can further observe the normal light still image at the same time.

If the operator selects the three-window mode B, the florescent light image is displayed as a still image, and the normal light image and the OCT image are displayed as animated images. In the normal light image, a cursor is displayed to indicate the OCT scanning line. By locating the cursor on a portion which might be diseased with monitoring the normal light image, the tip of the endoscope 1 can be located at the position suitable for observing the portion which might be diseased. At this stage, the OCT image corresponds to the portion where the cursor is located in the normal light image. As above, the operator can move the tip of the endoscope 1 with monitoring the animated normal light image, and can observe the OCT image at a desired position. It should be noted that the operator can further observe the fluorescent light still image at the same time.

As above, the operator can observe the normal light image, fluorescent light image and the OCT image at the same time. Accordingly, the operator can easily recognize which portion of the paries is being displayed as the OCT image accurately. Therefore, the accuracy of the diagnosis can be improved.

Further, the operator can find the early cancer, a relatively small tumor or the like using only the endoscope. Further, since the observation is done using the endoscope, a necessary treatment can be performed. That is, when a diseased portion is found, forceps, laser treatment instrument or the like can be inserted through the instrument channel of the endoscope, and an endoscopic treatment can be done, which reduce the burden to a patient.

The present disclosure relates to the subject matter contained in Japanese Patent Application No. HEI 11-237825, filed on Aug. 25, 1999, which is expressly incorporated herein by reference in its entirety.

What is claimed is:

1. An endoscope system, comprising:
    a normal light image capturing system that captures an image of an object inside a human cavity by illuminating the object with white light to the object;
    a fluorescent light image capturing system that captures image of the object by illuminating the object with excitation light, the object emits fluorescent light upon incidence of the excitation light;
    an OCT (Optical Coherence Tomography) image capturing system that captures an OCT image of a desired portion of the object;
    a displaying device; and
    a display controlling system that controls said displaying device to display the normal light image, the fluorescent light image and the OCT image simultaneously.

2. The endoscope system according to claim 1, wherein at least one of the normal light image and the fluorescent light image is displayed on said displaying device as an animated image.

3. The endoscope system according to claim 2, further comprising a OCT scanning line indicating system that indicates a line representative of a scanning line corresponding to the OCT image on one of the normal light image and the fluorescent light image displayed as the animated image.

4. The endoscope system according to claim 3, wherein the OCT image is displayed as an animated image.

5. An endoscope system, comprising:
    an illuminating optical system that selectively emits, toward an object, visible light and excitation light for exciting the object to fluoresce;
    an objective optical system that converges light from the surface of the object to form an optical image of the surface of the object;
    an image capturing system that captures an optical image of a surface of the object and generates an image signal corresponding to the optical image;
    a first light guide;
    a second light guide;
    an optical coupler for optically coupling said first and second light guides;
    a low-coherent light source that emits a low-coherent light beam, said low-coherent light source being provided at a proximal end side of one of said first and second light guides, the light emitted by said low-coherent light source being incident on said one of said first and second light guides;
    a scanning unit that causes the light beam emerged from said first light guide to scan on a predetermined surface of said object, said scanning unit directing the light beam reflected by the object to said first light guide as a detection light beam;
    a reflector that reflects a light beam emerged from said second light guide to said second light guide as a reference beam;
    an optical path length adjusting system that relatively changes a length of an optical path length from said optical coupler to said object via said first light guide and an optical path length from said optical coupler to said reflector via said second light guide;
    a light detecting device provided at a proximal end side of the other of said first and second light guides, said light detecting device detecting interfered beam generated due to interference between said reference beam and said detection beam; and
    an OCT image forming system that generates a tomogram based on the signal detected by said light detecting device when said optical path length adjusting system and said scanning unit operate; and
    a video signal generating system that generates video signals of the optical image of the object and the OCT image based on the image signal output by said image capturing system and said OCT image forming system.

6. The endoscope system according to claim 5, further comprising a display device that displays the optical image of the surface of the object and the OCT image in accordance with the video signals output by said video signal generating system.

7. The endoscope system according to claim 6,
    wherein said image capturing system generates a normal light image signal representing the surface of the object when said illuminating optical system emits the visible light toward the object,
    wherein said image capturing system generates a fluorescent light image signal representing the surface of the object when said illuminating optical system emits the excitation light toward the object,
    wherein said OCT image forming system outputs an OCT image signal representing the OCT image of the object, and
    wherein said video signal generating system generates video signals based on the normal image signals, fluorescent image signals and the OCT image signals, and causes said display device to display the normal light image, the fluorescent light image and the OCT image arranged in a predetermined manner.

8. The endoscope system according to claim 7, wherein said video signal generating system includes a memory corresponding to a screen of said display device, said memory storing the normal light image signal, the fluorescent light image signal and the OCT image signal.

9. The endoscope system according to claim 7, wherein said video signal generating system makes said display device display one of the normal light image and the fluorescent light image as an animated image, and wherein said video signal generating system makes said display device display the OCT image as an animated image.

10. The endoscope system according to claim 9, wherein said video signal generating system makes said display device display the other one of the normal light image and the fluorescent light image as a still image.

11. The endoscope system according to claim 7, wherein said video signal generating system makes said display device display the normal light image as a color image.

12. The endoscope system according to claim 7, wherein said video signal generating system includes a cursor generating system that inserts a cursor indicating a scanning position of said scanning unit in the normal light image or the fluorescent light image.

13. The endoscope system according to claim 5, further comprising:
   a visible light source that emits the visible light;
   an excitation light source that emits the excitation light; and
   a light source switching system that selectively causes the visible light and the excitation light to impinge on said illuminating optical system.

14. The endoscope system according to claim 5, wherein said optical path length adjusting system moves said reflector toward/away from a tip of said second light guide to vary the optical path length from said optical coupler to said reflector via said second light guide relative to the optical path length from said optical coupler to said object via said first light guide.

15. The endoscope system according to claim 5, wherein said low-coherent light source includes a super-luminous diode.

* * * * *